(12) United States Patent
Weiner et al.

(10) Patent No.: US 7,220,728 B2
(45) Date of Patent: *May 22, 2007

(54) METHODS OF INDUCING MUCOSAL IMMUNITY

(75) Inventors: David B. Weiner, Merion, PA (US); Bin Wang, Havertown, PA (US); Kenneth E. Ugen, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/076,900

(22) Filed: Feb. 14, 2002

(65) Prior Publication Data

US 2002/0142987 A1  Oct. 3, 2002

Related U.S. Application Data

(63) Continuation of application No. 08/357,398, filed on Dec. 16, 1994, now Pat. No. 6,348,449.

(51) Int. Cl.
*A61K 48/00* (2006.01)
*C12N 15/74* (2006.01)

(52) U.S. Cl. ..................... 514/44; 435/320.1
(58) Field of Classification Search ................. 514/44; 435/320.1; 424/93.2
See application file for complete search history.

(56) References Cited

U.S. PATENT DOCUMENTS

| | | | | |
|---|---|---|---|---|
| 4,224,404 A | 9/1980 | Viza et al. | | 435/2 |
| 4,394,448 A | 7/1983 | Szoka, Jr. et al. | | 435/172 |
| 4,806,463 A | 2/1989 | Goodchild et al. | | 435/5 |
| 4,945,050 A | 7/1990 | Sanford et al. | | 435/172.1 |
| 5,017,487 A | 5/1991 | Stunnenberg et al. | | 435/172.3 |
| 5,036,006 A | 7/1991 | Sanford et al. | | 435/170.1 |
| 5,185,254 A | 2/1993 | Linnenbach | | 435/172.3 |
| 5,264,618 A | 11/1993 | Felgner et al. | | 560/224 |
| 5,589,466 A | 12/1996 | Felgner et al. | | 514/44 |
| 5,593,972 A | 1/1997 | Weiner et al. | | 514/44 |
| 5,679,647 A | 10/1997 | Carson et al. | | 514/44 |
| 5,804,566 A * | 9/1998 | Carson et al. | | 514/44 |
| 6,214,804 B1 | 4/2001 | Felgner et al. | | 514/44 |
| 6,348,449 B1 * | 2/2002 | Weiner et al. | | 514/44 |

FOREIGN PATENT DOCUMENTS

| | | |
|---|---|---|
| WO | WO 90/11092 | 10/1990 |
| WO | WO 91/12329 | 8/1991 |
| WO | WO 93/17706 | 9/1993 |
| WO | WO 93/23552 | 11/1993 |
| WO | WO 94/16737 | 8/1994 |
| WO | WO 94/17792 | 8/1994 |
| WO | WO 94/23738 | 10/1994 |
| WO | WO95/11701 | 5/1995 |
| WO | WO95/30019 | 11/1995 |
| WO | WO 96/14876 | 5/1996 |

OTHER PUBLICATIONS

Wang et al, PNAS 1993;90:4156-60.*
Gately et al, Cell Immunol 1992;143:127-42.*
Sublingual: Merriam-Webster's Online dictionary, 2004.*
Harris et al, J Pharm Sci 1992;81:1-10.*
Acsadi et al., "Human Dystrophin Expression in Mdx Mice After Intramuscular Injection of DNA Constructs", *Nature* 352: 815-818 (1991).
Anderson, W. French, "Prospects for Human Gene Therapy," *Science* 226:401-409, 1984.
Benoit et al., "Destruction and regeneration of skeletal muscle after treatment with a local anaesthetic, bupivacaine (Marcaine®)," *J. Anat.* 107:547-556, 1970.
Benvenisty et al., "Direct introduction of genes into rats and expression of the genes," *Proc. Natl. Acad. Sci. USA*, 83:9551-9555, 1986.
Brandsma et al., "Use of a rapid, efficient innoculation method to induce papillomas by conttontail rabbit papillomavirus DNA shows that the E7 gene is required," *Proc. Natl. Acad. Sci. USA*, 88:4816-4820, 1991.
Brigham et al., "Rapid Communication: In Vivo Transfection of Murine Lungs with a Functioning Prokaryotic Gene Using A Liposome Vehicle," *American Journal of the Medical Sciences*, 298:278-281, 1989.
Butini, L. et al., "Comparative Analysis of HIV-Specific CTL Activity in Lymphoid Tissue and Peripheral Blood" J. of Cell Biochem. Suppl 18B:147 (Abstract J306 (1994).
Dubensky et al., "Direct transfection of viral and plasmid DNA into the liver of spleen of mice," *Proc. Natl. Acad. Sci. USA*, 81:7529-7533, 1984.
Felgner and Rhodes, "Gene Therapeutics" *Nature* 349: 351-352 (1991).
Fleckenstein et al., "Tumour induction with DNA of oncogenic primate herpesviruses," *Nature*, 274:57-59, 1978.
Friedmann et al., "Progress Toward Human Gene Therapy," *Science*, 244:1275-1281, 1989.
Hall-Craggs, E.C.B., "Rapid Degeneration and Regeneration of a Whole Skeletal Muscle Following Treatment with Bupivacain (Marcain)," *Experimental Neurology*, 43:349-358, 1974.
Haynes, B.F., "Scientific and Social Issues of Human Immunodeficiency Virus Vaccine Development" Science 260:1279-1286 (1993).

(Continued)

*Primary Examiner*—Q. Janice Li
(74) *Attorney, Agent, or Firm*—Pepper Hamilton LLP

(57) ABSTRACT

Methods of inducing mucosal immunity in individuals against proteins and peptides are disclosed. The methods comprise the step of administering topically or by lavage into mucosal tissue selected from the group consisting of rectal, vaginal, urethral, sublingual and buccal, a nucleic acid molecule that comprises a nucleotide sequence that encodes a protein or peptide that comprises an epitope against which mucosal immunity is desired. The methods may be used to immunize and individual against a pathogen infection, hyperproliferative diseases or autoimmune diseases using nucleic acid molecules which encode proteins and peptides that share an epitope with a pathogen antigen or protein associated with cells involved in hyperproliferative diseases or autoimmune diseases, respectively,

44 Claims, 2 Drawing Sheets

OTHER PUBLICATIONS

Howley, Peter M., "Papillomavirinae and Their Replication," *Virology*, Chapter 58:1625-1650, 1990.
Israel et al., "Biological Activity of Polyoma Viral DNA in Mice and Hamsters," *J. of Virology*, 29:990-996, 1979.
Kaneda et al., "Increased Expression of DNA Cointroduced with Nuclear Protein in Adult Rat Liver," *Science*, 243:375-378, 1989.
Klein et al., "Transformation of Microbes, Plants and Animals by Particle Bombardment," *Bio/Technology*, 10:286-291, 1992.
Knuth, A. et al., "Cellular and Humoral Immune Responses Against Cancer:Implications for Cancer Vaccines" Current Opinion in Immunology 3: 659-664 (1991).
Ledley, F.D., "Clinical Considerations in the Design of Protocols for Somatic Gene Therapy" Human Gene Therapy 2: 77-83 (1991).
Mayne et al., "Tumour Induction by Simian Adenovirus SA7 DNA Fragments," *Nature New Biology*, 232:182-183, 1971.
McCutchan et al., "Enhancement of the Infectivity of Simian Virus 40 Deoxyribonucleic Acid with Diethylaminoethyl-Dextran," *J. of the Nat. Cancer Institute*, 41:351-356, 1968.
Nabel et al., "Site-Specific Gene Expression in Vivo by Direct Gene Transfer into the Arterial Wall," *Science*, 249:1285-1288, 1990.
Nicolau et al., "In vivo expression of rat insulin after intravenous administration of the lipsome-entrapped gene for rat insulin I," *Proc. Natl. Acad. Sci. USA*, 80:1068-1072, 1983.
Orth et al., "Infectious and Oncogenic Effect of DNA Extracted from Cells Infected with Polyoma Virus," *P.S.E.B.M.*, 115:1090-1095, 1964.
Sol et al., "Oncogenicity of SV40 DNA in the Syrian Hamster," *J. gen. Vir.* 37:635-638, 1977.
Tang et al., "Genetic immunization is a simple method for eliciting an immune response," *Nature* 356:152-154, 1992.
Thomason et al., "Stable incorporation of a bacterial gene into adult rat skeletal muscle in vivo," *Cell Physiol.*, 27:C578-581, 1990.
Torpey, III, D. et al., "Effects of Adoptive Immunotherapy with Autologous $CD8_+$ T Lymphocytes on Immunologic Parameters: Lymphocyte Subsets and Cytotoxic Activity" Clinical Immunology and Immunopathology 68(3): 263-272 (1993).
Ulmer et al., "Heterologous Protection Against Influenza by Injection of DNA Encoding a Viral Protein," *Science*, 259:1745-1749, 1993.
Vitadello et al., "Gene Transfer in Regenerating Muscle," *J. of Cellular Biochemistry*, Suppl. 17E:252, Mar. 29-Apr. 25, 1993.
Wang, B. et al.,, "Gene Innoculation Generates Immune Responses Against Human Immundeficiency Virus Type 1" Proc. Natl. Acad. Sci. USA 90: 4156-4160 (1993).
Wells, D.J., "Improved Gene Transfer by Direct Plasmid Injection Associated with Regeneration in Mouse Skeletal Muscle" FEBS Letts 332(1,2) 179-182 (1993).
Will et al., "Cloned HBV DNA causes hepatitis in chimpanzees," *Nature*, 299:740-742, 1982.
Wolff et al., "Direct Gene Transfer into Mouse Muscle in Vivo" *Science* 247: 1465-1468 (1990).
Wolff et al., "Conditions Affecting Direct Gene Transfer Into Rodent Muscle In Vivo" *BioTechniques* 11: 474-485 (1991).
Wu et al., "Receptor-mediated Gene Delivery and expression in Vivo," *J. of Biological Chemistry*, 263:14621-14624, 1988.
Yang et al., "In vivo and in vitro gene transfer to mammalian somatic cells by particle bombardment," *Proc. Natl. Acad. Sci. USA*, 87:9568-9572, 1990.
Zelenin et al., "High-velocity mechanical DNA transfer of the chloramphenicolacetyl transferase gene into rodent liver, kidney and mammary gland cells in organ explants and in vivo," *FEBS Letts.*, 280:94-96, 1991.
Fynan, E.F. et al., "Use of DNA encoding influenza Hemagglutinin as an avian influenza vaccine", *DNA Cell Biol.*, 1993, 12(9), 785-789.
Staats, H.F. et al., "Mucosal immunity to infection with implications for vaccine development", *Curr. Opin. Immunol.*, 1994, 6, 572-583.
Fynan, et al., "DNA vaccines: protective immunizations by parental, mucosal, and gene-gun inoculations," Proc. Natl. Acad. Sci. USA (1993) 90:11478-11482.

\* cited by examiner

METHODS OF INDUCING MUCOSAL IMMUNITY

This application is a continuation of application Ser. No. 08/357,398 filed Dec. 16, 1994, which issued as U.S. Pat. No. 6,348,449 B1 on Feb. 19, 2002.

FIELD OF THE INVENTION

The present invention relates to methods for introducing genetic material into the cells of an individual. The methods of the invention can be used to deliver genetic material that encodes protein targets for immunization. The methods of the present invention induce mucosal immunity.

BACKGROUND OF THE INVENTION

The direct introduction of a normal, functional gene into a living animal has been studied as a means for replacing defective genetic information. In some studies, DNA is introduced directly into cells of a living animal without the use of a viral particle or other infectious vector. Nabel, E. G., et al., (1990) *Science* 249:1285–1288, disclose site-specific gene expression in vivo of a beta-galactosidase gene that was transferred directly into the arterial wall in mice. Wolfe, J. A. et al., (1990) *Science* 247:1465–1468, disclose expression of various reporter genes that were directly transferred into mouse muscle in vivo. Acsadi G., et al., (1991) *Nature* 352:815–818, disclose expression of human dystrophin gene in mice after intramuscular injection of DNA constructs. Wolfe, J. A., et al., 1991 *BioTechniques* 11(4):474–485, which is incorporated herein by reference, refers to conditions affecting direct gene transfer into rodent muscle in vivo. Felgner, P. L. and G. Rhodes, (1991) *Nature* 349: 351–352, disclose direct delivery of purified genes in vivo as drugs without the use of retroviruses.

The use of direct gene transfer as an alternative anti-pathogen vaccination method has been suggested. Use of direct gene transfer by single injection is suggested as a possible vaccination strategy against HIV. A cellular immune response to HIV gp120 resulting from introduction of plasmid DNA encoding the same into cells is reported to have been observed. PCT International Application Number PCT/US90/01515 published Oct. 4, 1990 discloses methods of immunizing an individual against pathogen infection by directly injecting naked polynucleotides into the individual's cells in a single step procedure. The use of transfecting agents other than lipofectins is specifically excluded from the disclosed methods. The stimulation of inoculated cells is neither disclosed nor suggested. An HIV vaccine is disclosed which consists of the introduction of polynucleotides that encode the viral protein gp120. The operability of this vaccine is not evidenced.

SUMMARY OF THE INVENTION

The present invention relates to methods of inducing mucosal immunity against proteins and peptides in an individual. The methods of the present invention comprise the step of administering by topical or lavage administration to mucosal tissue of an individual, a nucleic acid molecule that comprises a nucleotide sequence that encodes a desired peptide or protein. The mucosal tissue is selected from the group consisting of rectal, vaginal, urethral, sublingual and buccal.

The present invention relates to methods of immunizing an individual against pathogens. The methods comprise the step of inducing mucosal immunity against a pathogen antigen in an individual by administering by topical or lavage administration to the mucosal tissue of an individual, a nucleic acid molecule that comprises a nucleotide sequence that encodes a peptide which comprises at least an epitope identical or substantially similar to an epitope displayed on a pathogen antigen. The mucosal tissue is selected from the group consisting of rectal, vaginal, urethral, sublingual and buccal.

The present invention relates to methods of immunizing an individual against a hyperproliferative disease or an autoimmune disease. The methods comprise the steps of administering by topical or lavage administration to the mucosal tissue of said individual cells, a nucleic acid molecule that comprises a nucleotide sequence that encodes a peptide that comprises at least an epitope identical or substantially similar to an epitope displayed on a hyperproliferative disease-associated protein or an autoimmune disease-associated protein, respectively. The mucosal tissue is selected from the group consisting of rectal, vaginal, urethral, sublingual and buccal.

The present invention relates to pharmaceutical compositions which comprise a nucleic acid molecule and a suitable carrier or diluent for topical or lavage administration.

DETAILED DESCRIPTION OF THE INVENTION

Figure 1A:
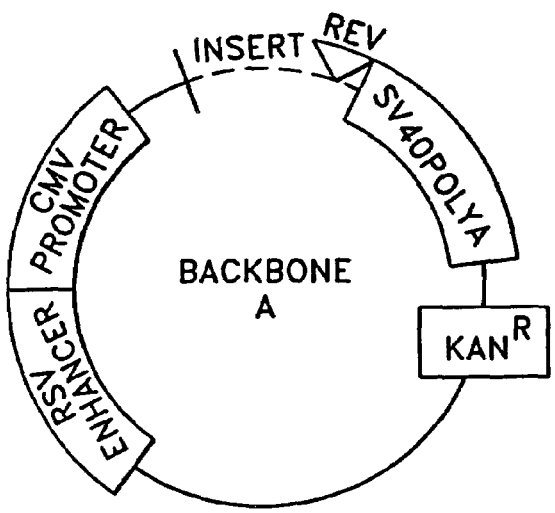
FIG. 1 is shows four backbones, A, B, C and D, used to prepare genetic construct.
Figure 1B:
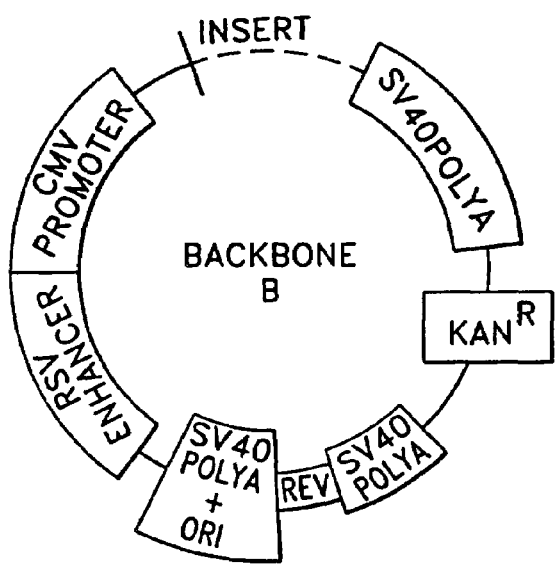
Figure 1C:
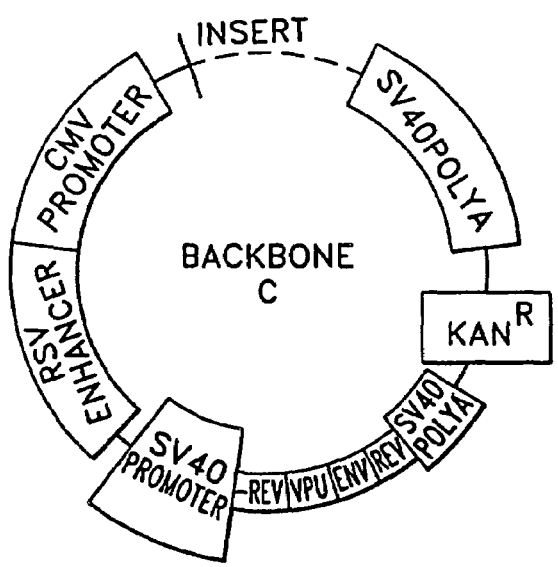
Figure 1D:
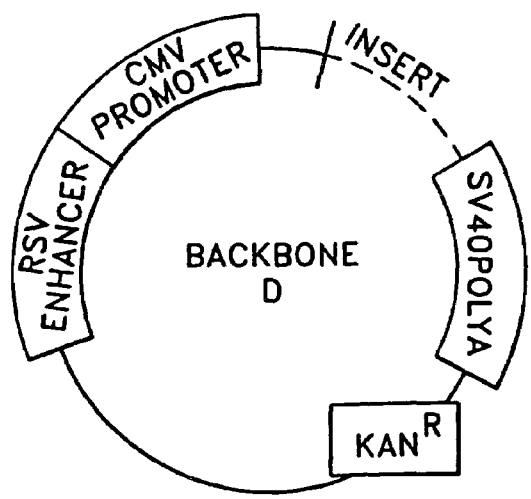
Figure 2A:
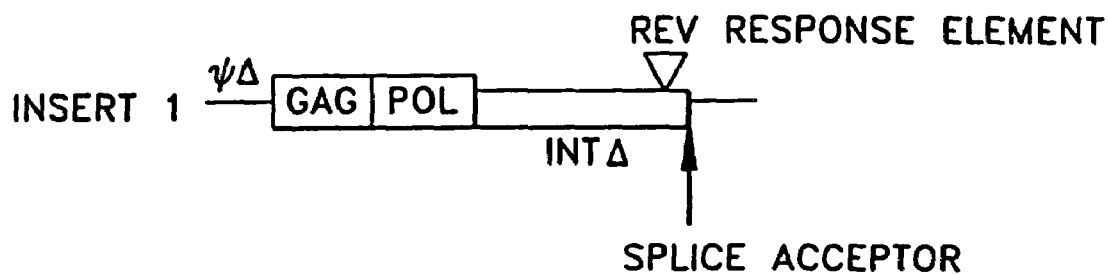
FIG. 2 shows four inserts, 1, 2, 3 and 4 which are inserted into backbones to produce genetic constructs.
Figure 2B:
Figure 2C:
Figure 2D:

The present invention relates to methods of introducing genetic material into the cells of an individual in order to induce mucosal immunity against proteins and peptides which are encoded by the genetic material. The methods comprise the steps of administering by topical or lavage administration to the mucosal tissue of said individual cells, a nucleic acid molecule that comprises a nucleotide sequence that either encodes a desired peptide or protein. The nucleic acid molecules are taken up by the cells in the mucosal tissue and a protein encoded by a nucleotide sequence of the molecule is expressed. The expression of the protein in the cells of the mucosal tissue results in the induction of a mucosal immune response.

The method of the present invention comprises the steps of administering nucleic acid molecules topically or by lavage to mucosal tissue selected from the group consisting of vaginal, rectal, urethral, buccal and sublingual.

Preferred embodiments of the present invention provide methods of delivering nucleic acid molecules to cells of an individual without the use of infectious agents. In some embodiments, the nucleic acid molecules are free from viral particles such as retroviral particles.

In some embodiments, the nucleic acid molecule is delivered to the cells in conjunction with administration of a polynucleotide function enhancer or a genetic vaccine facilitator agent. Polynucleotide function enhancers are described in U.S. Ser. No. 08/008,342 filed Jan. 26, 1993, U.S. Ser. No. 08/029,336 filed Mar. 11, 1993, U.S. Ser. No. 08/125,012 filed Sep. 21, 1993, and International Application Serial Number PCT/US94/00899 filed Jan. 26, 1994, which are each incorporated herein by reference. Genetic vaccine facilitator agents are described in U.S. Ser. No. 08/221,579 filed Apr. 1, 1994, which is incorporated herein by reference. The co-agents which are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid may also be used administered in conjunction with the genetic construct.

Nucleic acid molecules which are delivered to cells according to the invention may serve as genetic templates for proteins that function as prophylactic and/or therapeutic immunizing agents. In preferred embodiments, the nucleic acid the nucleic acid molecules comprise the necessary regulatory sequences for transcription and translation of the coding region in the cells of the animal.

According to the present invention, compositions and methods are provided which prophylactically and/or therapeutically immunize an individual against a pathogen or abnormal, disease-related cell. The genetic material encodes a peptide or protein that shares at least an epitope with an immunogenic protein found on the pathogen or cells to be targeted. The genetic material is expressed by the individual's cells and serves as an immunogenic target against which an immune response is elicited. The resulting immune response is broad based: in addition to a humoral immune response, both arms of the cellular immune response are elicited including mucosal immunity. The methods of the present invention are useful for conferring prophylactic and therapeutic immunity. Thus, a method of immunizing includes both methods of protecting an individual from pathogen challenge, or occurrence or proliferation of specific cells as well as methods of treating an individual suffering from pathogen infection, hyperproliferative disease or autoimmune disease.

The present invention is useful to elicit broad immune responses against a target protein, i.e. proteins specifically associated with pathogens or the individual's own "abnormal", cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

As used herein the term "desired protein" is meant to refer to peptides and protein encoded by gene constructs of the present invention which act as target proteins for an immune response.

According to the present invention, DNA or RNA that encodes a desired protein is introduced into the cells of mucosal tissue of an individual where it is expressed, thus producing the desired protein. The DNA or RNA encoding the desired protein is linked to regulatory elements necessary for expression in the cells of the individual. Regulatory elements for DNA expression include a promoter and a polyadenylation signal. In addition, other elements, such as a Kozak region, may also be included in the genetic construct.

As used herein, the term "genetic construct" refers to the DNA or RNA molecule that comprises a nucleotide sequence which encodes the desired protein and which includes initiation and termination signals operably linked to regulatory elements including a promoter and polyadenylation signal capable of directing expression in the cells of the vaccinated individual.

As used herein, the term "expressible form" refers to gene constructs which contain the necessary regulatory elements operable linked to a coding sequence that encodes a target protein, such that when present in the cell of the individual, the coding sequence will be expressed.

As used herein, the term "genetic vaccine" refers to a pharmaceutical preparation that comprises a genetic construct that comprises a nucleotide sequence that encodes a target protein including pharmaceutical preparations useful to invoke a prophylactic or therapeutic immune response.

As used herein, the term "target protein" refers to a protein against which an immune response can be elicited. The target protein is an immunogenic protein which shares at least an epitope with a protein from the pathogen or undesirable cell-type such as a cancer cell or a cell involved in autoimmune disease against which immunization is required. The immune response directed against the target protein will protect the individual against and treat the individual for the specific infection or disease with which the target protein is associated.

As used herein, the term "sharing an epitope" refers to proteins which comprise at least one epitope that is identical to or substantially similar to an epitope of another protein.

As used herein, the term "substantially similar epitope" is meant to refer to an epitope that has a structure which is not identical to an epitope of a protein but nonetheless invokes an cellular or humoral immune response which cross reacts to that protein.

Genetic constructs comprise a nucleotide sequence that encodes a desired protein operably linked to regulatory elements needed for gene expression. Accordingly, incorporation of the DNA or RNA molecule into a living cell results in the expression of the DNA or RNA encoding the desired protein and thus, production of the desired protein.

When taken up by a cell, the genetic construct which includes the nucleotide sequence encoding the desired protein operably linked to the regulatory elements may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication.

The molecule that encodes a desired protein may be DNA or RNA which comprise a nucleotide sequence that encodes the desired protein. These molecules may be cDNA, genomic DNA, synthesized DNA or a hybrid thereof or an RNA molecule such as mRNA. Accordingly, as used herein, the terms "DNA construct", "genetic construct" and "nucleotide sequence" are meant to refer to both DNA and RNA molecules.

The regulatory elements necessary for gene expression of a DNA molecule include: a promoter, an initiation codon, a stop codon, and a polyadenylation signal. In addition, enhancers are often required for gene expression. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments, the vector used is selected from those described in Example 11.

In some preferred embodiments related to immunization applications, the genetic construct contains nucleotide sequences that encode a target protein and further include genes for proteins which enhance the immune response against such target proteins. Examples of such genes are those which encode cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12. In some embodiments, it is preferred that the gene for GM-CSF is included in genetic constructs used in immunizing compositions.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

The genetic constructs used in the present invention are preferably not incorporated within retroviral particles. The genetic constructs are taken up by the cell without retroviral particle-mediated insertion such as that which occurs when retrovirus particles with retroviral RNA that is incorporated in retroviral particles infects a cell. As used herein, the term "free from retroviral particles" is meant to refer to genetic constructs that are not incorporated within retroviral particles. As used herein, "dissociated from an infectious agent" is meant to refer to genetic material which is not part of a viral, bacterial or eukaryotic vector, either active, inactivated, living or dead, that is capable of infecting a cell.

In some embodiments, the genetic constructs constitute less than a complete, replicatable viral genome such that upon introduction into the cell, the genetic construct possesses insufficient genetic information to direct production of infectious viral particles. As used herein, the term "incomplete viral genome" is meant to refer to a genetic construct which contains less than a complete genome such that incorporation of such a genetic construct into a cell does not constitute introduction of sufficient genetic information for the production of infectious virus.

In some embodiments, DNA molecules are delivered free from the precipitating agent $CaPO_4$.

In some embodiments, an attenuated viral vaccine may be delivered as a genetic construct which contains enough genetic material to allow for production of viral particles. Delivery of the attenuated vaccine as a genetic construct allows for an easier way to produce large quantities of safe, pure active immunizing product.

In some embodiments, the genetic constructs of the present invention are delivered to the cells of an individual free of solid particles or irritants.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhoea, listeria and shigella. In addition, the present invention is also useful to immunize an individual against protozoan pathogens which include a stage in the life cycle where they are intracellular pathogens. As used herein, the term "intracellular pathogen" is mean to refer to a virus or pathogenic organism that, at least part of its reproductive or life cycle, exists within a host cell and therein produces or causes to be produced, pathogen proteins. Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material which encodes immunogenic proteins against which a protective immune response can be mounted must be included in the genetic construct. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets. In addition, multiple inoculant which can be delivered to different cells in an individual can be prepared to collectively include, in some cases, a complete or, more preferably, an incomplete such as a near complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

The ease of handling and inexpensive nature of DNA and RNA further allow for more efficient means of screening for protective antigens. Genes can be sorted and systematically tested much more easily than proteins. The pathogenic agents and organism for which the vaccine is being produced to protect against is selected and an immunogenic protein is identified. Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HTLV or HBV.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a DNA construct that encodes at least one of these proteins will elicit an immune response that will target T cells involved in RA. See: Howell; M. D., et al., 1991 *Proc. Natl. Acad. Sci. USA* 88:10921–10925; Paliard, X., et al., 1991 *Science* 253: 325–329; Williams, W. V., et al., 1992 *J. Clin. Invest.* 90:326–333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wucherpfennig, K. W., et al., 1990 *Science* 248:1016–1019; Oksenberg, J. R., et al., 1990 *Nature* 345:344–346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

According to the present invention, the genetic construct is administered to cells of mucosal tissue of an individual by topically or by lavage. For intravaginal administration, genetic constructs may be formulated as a cream, ointment, salve, douche or suppository. For intravaginal administration, genetic constructs may be formulated as a cream, ointment, salve, enema or suppository.

Lavage and topical administration of pharmaceutical compositions are well known. One having ordinary skill in the art can, following the teachings herein, use lavage or topical administration protocols to deliver genetic material to mucosal cells of an individual and induce mucosal immunity in the individual. Mucosal tissues include sublingual, buccal, urethral, rectal and vaginal tissues. The methods of the present invention are particularly useful to deliver genetic material intravaginally.

The genetic vaccines according to the present invention comprise about 1 nanogram to about 1000 micrograms of DNA. In some preferred embodiments, the vaccines and therapeutics contain about 10 nanograms to about 800 micrograms of DNA. In some preferred embodiments, the vaccines and therapeutics contain about 0.1 to about 500 micrograms of DNA. In some preferred embodiments, the vaccines and therapeutics contain about 1 to about 350 micrograms of DNA. In some preferred embodiments, the vaccines and therapeutics contain about 25 to about 250 micrograms of DNA. In some preferred embodiments, the vaccines and therapeutics contain about 100 micrograms DNA.

The genetic vaccines according to the present invention are formulated using standard components for topical or lavage administration. *Remington's Pharmaceutical Sciences* 18th Edition 1990, Alfonso R. Gennaro, Ed. Mack Publishing Co. Easton Pa. 18042, which is incorporated herein by reference, teaches formulation of compositions adapted for topical administration, suppository administration or lavage administration useful in the methods of the present invention. One having ordinary skill in the art can readily formulate a pharmaceutical composition that comprises a genetic construct. Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation. The pharmaceutical preparations according to the present invention are preferably provided sterile and pyrogen free.

One of skill in the art of pharmaceutical formulations, e.g., having an advanced degree in Pharmaceutics or Pharmaceutical Sciences, can prepare a variety of appropriate dosage forms and formulations for the compositions of the invention with no more than routine experimentation. A number of texts in the field, a,g., *Remington's Pharmaceutical Sciences and The U.S. Pharmacopoeia/National Formulary*, latest editions, provide considerable guidance in this respect.

A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

In addition to the usual considerations of stability and bioavailability, in order to achieve adequate mucosal immunity, the dosage form will provide adequate physical and temporal contact with the selected mucosa. The active ingredients) can be formulated as a single phase or two-phase system, and in liquid, solid or semisolid dosage form, for example, cream, gel, emulsion, suspension, ointment, suppository, tablet. The formulation vehicle may be aqueous, oleaginous, or an oil-in-water or water-in-oil emulsion, preferably water/oil. Although the active ingredients may be formulated in sterile water or saline, a liquid formulation will preferably have adequate viscosity to be retained in contact with the selected mucosal surfaces for minutes to hours to allow adequate drug penetration and cellular uptake, One preferred dosage form for application of the compositions of the invention to the vaginal, rectal or urethral mucosa is the suppository. Suppositories are solid dosage forms of various shapes, sizes and compositions designed for introduction into the rectal, vaginal, or urethral orifice of the human body. They usually soften, melt, or dissolve at body temperature. Usual suppository bases include theobroma oil (cocoa butter), glycerinated gelatin, hydrogenated vegetable ails, mixtures of polyethylene glycols of various molecular weights, and fatty acid esters of polyethylene glycol. Cocoa butter is a suitable diluent or vehicle for suppositories because it melts quickly at body temperature and permits the ionized form of the drugs of the invention to diffuse into the mucosa; however, oleaginous vehicles are usually not preferred for vaginal suppositories because of the nonabsorbable residue formed. On the other hand glycerinated gelatin is seldom used rectally because of its slow dissolution.

Gels are useful pharmaceutical formulations for administration of the polynucleotide compositions of the invention, either alone or in admixture with a polynucleotide uptake/expression facilitator, to various mucosal tissues of the human or animal body, including the buccal or sublingual mucosa, as well as the rectal, vaginal, or urethral mucosa.

Useful gel formulations can be made using Carbopo® 934 or Carbopol® 940 (polyacrylate polymer) at a final concentration of 0.5% w/v (BF Goodrich); polyvinylalcohol MW 72,000 or 49,000 at a final concentration of 4% w/v; or Povidone® K30; Povidone® K60; or Povidone® K90 (polyvinylpyrrolidone) at a final concentration of 1.5 to 3% w/v, in an aqueous buffer solution of 2 mM EDTA, 40 mM Tris, pH 7.5. The polynucleotide composition should be present at a concentration that will permit a convenient volume of gel to be used, as appropriate for the selected mucosal surface, e.g., a concentration wherein about 0.5 to about 5 ml of gel can be used to deliver between 0.1 mcg to about 1 mg of DNA, preferably between about 1 to about 500 mcg of DNA, more preferably about 25 to about 250 mcg of DNA. For example, with a gel having a concentration of 100 mcg of DNA per ml, a dose of between 1 and 5 mls can be used to deliver a dose of 100 to mcg to 500 mcg to the vaginal or rectal mucosa. A polynucleotide uptake/expression facilitator such as bupivacaine or a functionally equivalent compound may optionally be present in the gel composition at an effective concentration, preferably between 0.1 and 0.5%.

Useful pharmaceutical dosage forms for administration of the polynucleotide compositions of the invention, either alone or in admixture with a polynucleotide uptake/expression facilitator, to various mucosal tissues of the human or animal body can be illustrated as follows:

A composition suitable, for administration as a rectal suppository is prepared by dispersing 500 mcg of finely divided medicinal substance, and optionally 25 mg of bupivacaine, HCl, into 2 g of solid cocoa butter at room temperature and suitably shaping the resulting mass, or by working with the oil in the melted state and allowing the resulting suspension to cool in a mold of suitable shape. Rectal suppositories are usually tapered at one or both ends and weigh about 2 g. A suitable quantity of hardening agent, such as wax, may be added to raise the melting point of the mixture in warm climates where cooling systems are not available; provided, however, that the resulting mixture must melt at body temperature.

A composition suitable for administration in vaginal suppository form 1a prepared by weighing 2 mg of finely divided polynucleotide medicinal substance into a tared container, adding 10 ml of 0.5% bupivacaine HCl in purified water, to make a total of 10 g, and dissolving or mixing depending on the solubility of the medicinal substance; 70 g of glycerin is added and mixed; 20 g of granular gelatin is then added and the composition heated carefully on a steam bath until the gelatin is dissolved. The melted mixture is is poured into chilled molds to yield 20 vaginal suppositories of 6 grams each containing 100 mcg of polynucleotide medicinal substance in admixture with 2.5 mg bupivacaine.

A vaginal tablet or insert composition is prepared containing 250 meg of finely divided polynucleotide medicinal substance in a tablet composition comprising lactose, microcrystalline cellulose, lactic acid, cornstarch, crospovidone, calcium lactate, magnesium stearate, silicone dioxide, and hydroxypropylmethylcellulose.

One gram (1 g) of Carbopol® 934 (polyacrylate polymer) (BF Goodrich) is added to 100 ml of purified water using a powder addition funnel and mixed using a low shear, high speed mechanical mixer to form a stiff homogeneous gel having a Carbopol concentration of 1% (w/v). Twenty mg DNA of the invention is added to 100 ml of an aqueous buffer solution (pH 7.6) containing 2 mM EDTA and 40 mM Tris. The DNA containing buffer and the Carbopol gel are mixed at low shear to yield a homogeneous gel containing 100 mcg DNA per ml. A polynucleotide uptake/expression facilitator such as bupivacaine HCl may be added at a concentration of about 0.1% to about 0.5% (w/v). The gel may be applied topically to buccal, sublingual, rectal, vaginal, and/or urethral mucosal surfaces.

In some embodiments of the invention, the individual is subject to a single administration to produce a full, broad immune response. In some embodiments of the invention, the individual is subject to a series of vaccinations to produce a full, broad immune response. According to some embodiments of the invention, at least two and preferably four to five administrations are given over a period of time. The period of time between administrations may include from 24 hours apart to two weeks or longer between administrations, preferably one week apart.

The methods of the present invention are useful in the fields of both human and veterinary medicine.

The Examples set out below include representative examples of aspects of the present invention. The Examples are not meant to limit the scope of the invention but rather serve exemplary purposes. In addition, various aspects of the invention can be summarized by the following description.

However, this description is not meant to limit the scope of the invention but rather to highlight various aspects of the invention. One having ordinary skill in the art can readily appreciate additional aspects and embodiments of the invention.

EXAMPLES

Example 1

The following is a list of constructs that are each described in U.S. Ser. No. 08/008,342 filed Jan. 26, 1993, U.S. Ser. No. 08/029,336 filed Mar. 11, 1993, U.S. Ser. No. 08/125,012 filed Sep. 21, 1993, International Application Serial Number PCT/US94/00899 filed Jan. 26, 1994, and/or U.S. Ser. No. 08/221,579 filed Apr. 1, 1994, the disclosures of which are each incorporated herein by reference. The present invention may be practiced by administering a genetic construct such as those incorporated herein by topical or lavage administration.

The vector pBabe.puro, which is used as a starting material to produce many of the below listed constructs, was originally constructed and reported by Morgenstern, J. P. and H. Land, 1990 *Nucl. Acids Res.* 18(12):3587–3596, which is incorporated herein by reference. The pBabe.puro plasmid is particularly useful for expression of exogenous genes in mammalian cells. DNA sequences to be expressed are inserted at cloning sites under the control of the Moloney murine leukemia virus (Mo MULV) long terminal repeat (LTR) promoter. The plasmid contains the selectable marker for puromycin resistance.

Plasmid pBa.Vα3 is a 7.8 kb plasmid that contains a 2.7 kb EcoRI genomic fragment encoding the T cell receptor Va3 region containing the L, V and J segments cloned into the EcoRI site of pBabe.puro. The T cell receptor-derived target protein is useful in the immunization against and treatment of T cell mediated autoimmune disease and clonotypic T cell lymphoma and leukemia.

Plasmid pBa.gagpol-vpr is a 9.88 kb plasmid that contains the gag/pol and vif genes from HIV/MN cloned into pBabe.puro. The vpr gene is deleted. The plasmid which contains these HIV viral genes, which encode HIV target proteins, is useful in the immunization against and treatment of HIV infection and AIDS.

Plasmid pM160 is an 11.0 kb plasmid that contains the 2.3 kb PCR fragment encoding the HIV-I/3B envelope protein and rev/tat genes cloned into pMAMneoBlue. The nef region is deleted. The plasmid which contains these HIV viral genes, which encode HIV target proteins, is useful in the immunization against and treatment of HIV infection and AIDS.

Plasmid pBa.VL is a 5.4 kb plasmid that contains PCR fragment encoding the VL region of an anti-DNA antibody cloned into pBabe.puro at the XbaI and EcoRI sites. The antibody-derived target protein is an example of a target protein useful in the immunization against and treatment of B cell mediated autoimmune disease and clonotypic B cell lymphoma and leukemia.

Plasmid pOspA.B is a 6.84 kb plasmid which contains the coding regions encoding the OspA and OspB antigens of the *Borrelia burgdorferi*, the spirochete responsible for Lyme's disease cloned into pBabe.puro at the BamHI and SalI sites. The plasmid which contains these pathogen genes, which encode target proteins, is useful in the immunization against Lyme's disease.

Plasmid pBa.Rb-G is a 7.10 kb plasmid which contains a PCR generated fragment encoding the rabies G protein cloned into pBabe.puro at the BamHI site. The plasmid which contains this pathogen gene, which encodes the rabies G protein, is useful in the immunization against Rabies.

Plasmid pBa.HPV-L1 is a 6.80 kb plasmid which contains a PCR generated fragment encoding the L1 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby.

Plasmid pBa.HPV-L2 is a 6.80 kb plasmid which contains a PCR generated fragment encoding the L2 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby.

Plasmid pBa.MNp7 is a 5.24 kb plasmid which contains a PCR generated fragment encoding the p7 coding region including the HIV MN gag (core protein) sequence cloned into pBabe.puro at the BamHI site. The plasmid which contains these HIV viral genes, which encode HIV-target proteins, is useful in the immunization against and treatment of HIV infection and AIDS.

Plasmid pGA733-2 is a 6.3 kb plasmid that contains the GA733-2 tumor surface antigen cloned from the colorectal carcinoma cell line SW948 into pCDM8 vector (Seed, B. and A. Aruffo, 1987 *Proc. Natl. Acad. Sci. USA* 84:3365, which is incorporated herein by reference) at BstXI site. The tumor-associated target protein is an example of a target protein useful in the immunization against and treatment of hyperproliferative disease such as cancer. The GA733-2 antigen is a useful target antigen against colon cancer.

Plasmid pT4-pMV7 is a 11.15 kb plasmid that contains CDNA which encodes human CD4 receptor cloned into pMV7 vector at the EcoRI site. The CD4 target protein is useful in the immunization against and treatment of T cell lymphoma.

Plasmid pDJGA733 is a 5.1 kb plasmid that contains the GA733 tumor surface antigen cloned into pBabe.puro at the BamHI site. The tumor-associated target protein is an example of a target protein useful in the immunization against and treatment of hyperproliferative disease such as cancer. The GA733 antigen is a useful target antigen against colon cancer.

Plasmid pBa.RAS is a 6.8 kb plasmid that contains the ras coding region that was first subcloned from pZIPneoRAS and cloned into pBabe.puro at the BamHI site. The ras target protein is an example of a cytoplasmic signalling molecule.

Plasmid pBa.MNp55 is a 6.38 kb plasmid which contains a PCR generated fragment encoding the p55 coding region including the HIV MN gag precursor (core protein) sequence cloned into pBabe.puro at the BamHI site. The plasmid which contains these HIV viral genes, which encode HIV target proteins, is useful in the immunization against and treatment of HIV infection and AIDS.

Plasmid pa.MNp24 is a 5.78 kb plasmid which contains a PCR generated fragment from the pMN-SF1 template encoding the p24 coding region including the whole HIV MN gag coding region cloned into pBabe.puro at the BamHI and EcoRI sites. The plasmid which contains these HIV viral genes, which encode HIV target proteins, is useful in the immunization against and treatment of HIV infection and AIDS.

Plasmid pBa.MNp17 is a 5.5 kb plasmid which contains a PCR generated fragment encoding the p17 coding region including the HIV MN gag (core protein) sequence cloned into pBabe.puro at the BamHI and EcoRI sites. The plasmid which contains these HIV viral genes, which encode HIV target proteins, is useful in the immunization against and treatment of HIV infection and AIDS.

Plasmid pBa.SIVenv is a 7.8 kb plasmid which contains a 2.71 PCR generated fragment amplified from a construct containing SIV 239 in pBR322 cloned into pBabe.puro at the BamHI and EcoRI sites.

Plasmid pcTSP/ATK.env is a 8.92 kb plasmid which contains a PCR generated fragment encoding the complete HTLV envelope coding region from HTLV-1/TSP and /ATK isolates subcloned into the pcDNA1/neo vector. The HTLV env target protein is useful in the immunization against and treatment of infection by HTLV and T cell lymphoma.

Plasmid pBa.MNgp160 is a 7.9 kb plasmid which contains a 2.8 kb PCR generated fragment amplified from a construct containing MNenv in pSP72 and cloned into pBabe.puro at the BamHI and EcoRI sites. The plasmid which contains these HIV viral genes, which encode HIV target proteins, is useful in the immunization against and treatment of HIV infection and AIDS.

Plasmid pC.MNp55 is a 11.8 kb plasmid which contains a 1.4 kb PCR generated fragment amplified from the gag region of MN isolate and cloned into the pCEP4 vector. The plasmid which contains these HIV viral genes, which encode HIV target proteins, is useful in the immunization against and treatment of HIV infection and AIDS.

Plasmid pC.Neu is a 14.2 kb plasmid that contains a 3.8 kb DNA fragment containing the human neu oncogene coding region that was cut out from the LTR-2/erbB-2 construct and subcloned into the pCEP4 vector. The neu oncogene target protein is an example of a growth factor receptor useful as a target protein for the immunization against and treatment of hyperproliferative disease such as cancer; in particular, colon, breast, lung and brain cancer.

Plasmid pC.RAS is a 11.7 kb plasmid that contains a 1.4 kb DNA fragment containing the ras oncogene coding region that was first subcloned from pZIPneoRAS and subcloned into pCEP4 at the BamHI site. The ras target protein is an example of a cytoplasmic signalling molecule. Ras encoding plasmid are useful for the immunization against and treatment of hyperproliferative disease such as cancer; in particular, ras related cancer such as bladder, muscle, lung, brain and bone cancer.

Plasmid pNLpuro is a 15 kb plasmid which contains HIV gag/pol and SV40-puro insertion. The plasmid which contains these HIV viral genes which encode HIV target proteins, is useful in the immunization against and treatment of HIV infection and AIDS.

Example 2

The present invention provides an HIV vaccine using direct genetic immunization. Genetic constructs are provided which, when delivered into the cells of an individual, are expressed to produce HIV proteins. According to some embodiments, the production of all viral structural proteins in the cells of the individual elicit a protective immune response which protects against HIV infection. The HIV vaccine of the present invention may be used to immunize uninfected individuals from HIV infection or serve as an immunotherapeutic for those individuals already infected. The HIV vaccine of the present invention invokes an immune response including CTLs which recognize and attack HIV infected cells and recognize the widest contingent of HIV protein. Thus, uninfected individuals are protected from HIV infection.

A genetic construct according to the present invention is not provided with a full complement of HIV genes. One or more essential genes can be deleted or intentionally altered to ensure that an infectious viral particle cannot be formed.

The DNA construct in a preferred embodiment consists of a promoter, an enhancer and a polyadenylation signal. The promoter may be selected from the group consisting of: HIV LTR, human Actin, human Myosin, CMV, RSV, Moloney, MMTV, human Hemoglobin, human muscle creatine and EBV. The enhancer may be selected from the group consisting of: human Actin, human Myosin, CMV, RSV, human Hemoglobin, human muscle creatine and EBV. The polyadenylation signal may be selected from the group consisting of: LTR polyadenylation signal and SV40 polyadenylation signal, particularly the SV40 minor polyadenylation signal among others.

In some embodiments of the present invention, about 0.1 to about 1000 micrograms, preferably about 1 to about 500 microgram, more preferably, about 25 to about 250 micrograms, most preferably, about 100 micrograms of DNA are administered.

In some embodiments, compositions to be administered include at least one of the following genetic constructs.

Plasmids and Cloning Strategies:

Two plasmids were constructed: one which contains HIV gag/pol and the other which contains HIV env.

The HIV-1 genomic clone pNL43 was obtained through the NIH AIDS Research and Reference Reagent Program (ARRRP), Division of AIDS, NIAID, NIH, from Dr. Malcolm Martin, and can be used as the starting material for HIV-1 viral genes for genetic constructs. Alternatively, any HIV molecular clone of infected cell can, through use of the polymerase chain technology, be modified sufficiently for construction including the HXB2 clone the MN clone as well as the SF or BAL-1 clone. The pNL43 clone is a construct that consists of HIV-1 proviral DNA plus 3 kb of host sequence from the site of integration cloned into pUC18.

Construction of pNL-puro-env⁻ plasmid:

This plasmid was constructed for expression of gag pol. The StuI site within the non-HIV 5' flanking human DNA of pNL43 was destroyed by partial digestion with StuI followed by digestion of the free ends with E. coli polymerase 1. The linear plasmid was filled and then self ligated, leaving a unique StuI site within the HIV genome. This plasmid, pNLDstu, was then digested with the blunting enzymes StuI and BsaBI which eliminated a large section of the coding sequence for gp120. The SV40 promoter and puromycin resistance coding region (puromycin acetyl transferase (PAC)) were isolated from pBABE-puro (Morgenstern and Land, 1990 Nucl. Acids Res. 18(12):3587–3596, which is incorporated herein by reference, kindly provided by Dr. Hartmut Land of the Imperial Cancer Research Fund) using EcoRI and ClaI. This fragment was blunted, then cloned into the StuI/BsaBI-digested pNLDstu. A clone was selected with the SV40-puro fragment in the correct orientation so that the 3' LTR of HIV could provide poly A functions for the PAC message. This plasmid was designated pNLpuro.

Cloning strategy for deletion of vpr regulatory gene from the HIV gag pol vector:

A region from just upstream of the unique PflMI site to just after the vif termination codon was amplified via PCR using primers that introduced a non-conservative amino acid change (glu->val) at amino acid 22 of vpr, a stop codon in the vpr reading frame immediately after amino acid 22, and an EcoRI site immediately following the new stop codon. This PCR fragment was substituted for the PflMI-EcoR I fragment of pNLpuro or pNL43. This substitution resulted in the deletion of 122 nucleotides of the open reading frame of vpr, thus eliminating the possibility of reversion that a point mutation strategy entails. The resulting plasmids, pNLpuroΔvpr, encode the first 21 natural amino acids of vpr plus a valine plus all other remaining HIV-1 genes and splice junctions in their native form. Such deletion strategy would also be applicable to nef, vif, and vpu and allow for structural gene expression but protect from the generation of a live recombinant virus. Plasmid construction for envelope expression:

The DNA segment encoding the envelope gene of HIV-1 HXB2 was cloned by the polymerase chain reaction (PCR) amplification technique utilizing the lambda cloned DNA obtained from the AIDS Research and Reference Reagent Program. The sequences of the 5' and 3' primers are 5'-AG-GCGTCTCGAGACAGAGGAGAGCAAGAAATG-3' (SEQ ID NO:1) with incorporation of XhoI site and 5'-TTTCCCTCTAGATAAGCCATCCAATCACAC-3' (SEQ ID NO: 2) with incorporation of XbaI site, respectively, which encompass gp160, tat and rev coding region. Gene specific amplification was performed using Taq DNA polymerase according to the manufacturer's instructions (Perkin-Elmer Cetus Corp.). The PCR reaction products were treated with 0.5 µg/ml proteinase K at 37° C. for thirty minutes followed by a phenol/chloroform extraction and ethanol precipitation. Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAMneoBlue (Clontech Laboratories, Inc., Palo Alto, Calif.). The resulting construct was designated as pM160E. The plasmid DNA was purified with CsCl gradient ultracentrifugation. The DNA construct pM160 encodes the HIV-1/HXB2 (Fisher, A. G., et al., (1985) *Nature* 316:262–265) gp160 membrane bound glycoprotein under control of a RSV enhancer element with the MMTV LTR as a promoter. An alternative envelope expression plasmid construction called HIV-1 env-rev plasmid:

The region encoding the two exons of rev and the vpu and envelope open reading frames of HIV-1 HXB2 was amplified via PCR and cloned into the expression vector pCNDA/neo (Invitrogen). This plasmid drives envelope production through the CMV promoter.

Production and Purification:

The plasmid in *E. coli* (DH5 alpha) is grown up as follows: An LE plus ampicillin agar plate is streaked with the desired plasmid culture from frozen stock. The plate is incubated overnight (14–15 hours) at 37° C. A single colony is taken from the plate and inoculated into 15 ml of LB medium with a peptone preparation and 50 µg/ml ampicillin. This culture is grown at 37° C. while being shaken (ca. 175 rpm) for 8–10 hours. $OD_{600}$ readings should be at least 1.0. 1 liter of LB medium with peptone and 50 µg/ml ampicillin is inoculated with 1.0 OD of culture. These 1–2 liter cultures are grown overnight at 37° C. while being shaken (175 rpm).

Plasmid grown in *E. coli* (strain DRS alpha) are harvested and purified by the following methods. General procedures for the lysis of cells and purification of plasmid can be found in "Molecular Cloning: A Laboratory Manual", 2nd Edition, J. Sambrook, E. F. Fritsch, and T. Maniatis, Cold Spring Harbor Press, 1989. The cells are concentrated and washed with glucose-tris-EDTA pH 8.0 buffer. The concentrated cells are lysed by treatment with lysozyme and briefly treated with 0.2 N KOH, the pH is then adjusted 5.5 with potassium acetate/-acetic acid buffer. Insoluble material is removed by centrifugation. To the supernatant is added 2-propanol to precipitate the plasmid. The plasmid is redissolved in tris-EDTA buffer and further purified by phenol/chloroform extraction and an additional precapitation with 2-propanol.

Endotoxin can optionally be removed by a variety of methods including the following: specific adsorption by immobilized materials such as polymyxin (Tani et al., *Biomater. Artif. Cells Immobilization Biotechnol.* 20(2–4): 457–62 (1992); Issekutz, *J. Immunol. Methods* 61(3):275–81 (1983)); anti-endotoxin monoclonal antibodies, such as 8A1 and HA-1A™ (Centocor, Malvern, Pa.; Bogard et al. *J. Immunol.* 150(10):4438–4449 (1993); Rietschel et al., *Infect. Immunity* page 3863 (1993)); positively charged depth filters (Hou et al., *J. Parenter. Sci. Technol.* 44(4):204–9 (Jul-Aug 1990)); poly(gamma-methyl L-glutamate), Hirayama et al., *Chem. Pharm. Bull. (Tokyo)* 40(8):2106–9 (1992)); histidine (Matsumae et al., *Biotechnol. Appl. Biochem.* 12:(2):129–40 (1990)); hydrophobic interaction columns and membranes (Aida et al., *J. Immunol Methods* 132(2):191–5 (1990); Umeda et al., *Biomater Artif Cells Artif Organs* 18(4):491–7 (1990); Hou et al., *Biochem. Biophys. Acta* 1073(1):149–54 (1991); Sawada et al., *J. Hyg. (London)* 97(1):103–14 (1986)); specific hydrophobic resins useful for removing endotoxin including hydrophobic polystyrene/divinylbenzene or divinylbenzene resins such as Brownlee Polypore Resin (Applied Biosystems, Palo Alto, Calif.); XUS 40323.00 (Dow Chemical, Midland, Mich.); HP20, CHP20P (Mitsubishi Kasei, U.S.); Hamilton PRP-1, PRP-infinity (Hamilton, Reno, Nev.); Jordi Reversed-Phase DVB, Jordi Gel DVB, Polymer Labs PLgel™ (Alltech, Deerfield, Ill.); Vydac PLx™ (Separations Group, Hesperia, Calif.); other endotoxin removing materials and methods include Detoxi-Gel™ Endotoxin Removing Gel (Pierce Chemical, Rockford, Ill.); Application Note 206, (Pharmacia Biotech Inc, Piscataway, N.J.). See also generally, Sharma, *Biotech. App. Biochem.* 8:5–22 (1986). Preferred anti-endotoxin monoclonal antibodies bind to the conserved domains of endotoxin, preferably antibodies to lipid A, the most structurally conserved portion of the endotoxin molecule. Such anti-lipid A monoclonal antibodies include the high affinity murine IgG monoclonal antibody 8A1 and the human anti-lipid A IgM(k) monoclonal antibody HA-1A™. HA-1A™ was derived from a human B *E. coli* J5 vaccine. HA-1A™. HA-1A™ is reported to be broadly cross-reactive with a variety of bacterial endotoxins (lipopolysaccharides).

Example 3

In another construction for expressing the env gene, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV env coding region is placed under the regulatory control of the CMV promoter and SV40 polyadenylation site. The HIV env coding region was obtained as a 2.3 kb PCR fragment form HIV/3B, Genebank sequence K03455. The resulting pCEP4-based plasmid, pRA-100, is maintained extrachromosomally and produces gp160 protein.

Example 4

In another construction for expressing the env gene, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV env coding region is placed under the regulatory control of the RSV promoter and SV40 polyadenylation site. The HIV env coding region was obtained as a 2.3 kb PCR fragment form HIV/3B, Genebank sequence K03455. The resulting pCEP4-based plasmid, pRA-101, is maintained extrachromosomally and produces gp160 protein.

Example 5

In another construction for expressing the gag/pol genes, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pCEP4-based plasmid, pLA-100, is maintained extrachromosomally and produces GAG55, reverse transcriptase, protease and integrase proteins.

Example 6

In another construction for expressing the gag/pol genes, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pREP4-based plasmid, pLA-101, is maintained extrachromosomally and produces GAG55, reverse transcriptase, protease and integrase proteins.

Example 7

The following construction, referred to herein as pGAGPOL.rev, is useful to express HIV gag/pol genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pGAGPOL.rev include a sequence that encodes p17, p24, and p15 of the gag open reading frame; a sequence that encodes protease, a sequence that encodes reverse transcriptase which contains a small deletion and a sequence that encodes the inactive amino terminus of integrase of the pol open reading frame; and a sequence that encodes rev. Each of the HIV sequences are derived from HIV-1 strain HXB2.

Several safety features are included in pGAGPOL.rev. These include use of the CMV promoter and a non-retroviral poly(A) site. Furthermore, deletion of the ψ sequence limits the ability to package viral RNA. In addition, multiple mutations of the reverse transcriptase yield an enzymatically inactive product. Moreover, a large deletion of integrase yields an inactive product and a Kanamycin resistance marker is used for stabilizing bacterial transformants.

Plasmid pGAGPOL.rev is constructed as follows.

Step 1. A subclone of part of the XIV-1 (HXB2) genome that is cloned into Bluescript (Stratagene) is used. The subclone of HIV-1 contains the complete 5'LTR and the rest of the HIV-1 genome to nucleotide 5795 (Genebank numbering). The HIV-1 sequences are obtained from the HXB2D plasmid (AIDS Repository).

Step 2. PCR part of gag from the open reading frame HXB2D plasmid (AIDS Repository). Cut PCR fragment with NotI and SpeI and ligate with HIV-1 subclone described above restricted with NotI and SpeI.

Step 3. PCR gag/pol junction and part of pol-encoding sequences from the HXB2D plasmid (AIDS Repository) with primers SEQ ID NO:3 and SEQ ID NO:4. Cut PCR product with ClaI and ligate together. Cut ligated fragments with BcII and SalI and ligate with plasmid from Step 2 digested with Bc-II and SalI.

Step 4. Cut plasmid from Step 3 with BspMI and EcoRI and religate with adapters formed by annealing linkers SEQ ID NO:5 and SEQ ID NO:6.

Step 5. Cut plasmid from Step 4 with NotI and SalI and ligate with plasmid from either 4a or 4b in description written for pENV (below). Cut also with NotI and SalI.

Step 6. Restrict plasmid from Step 5 with SalI and MluI and ligate with PCR product obtained by PCR of rev with primers SEQ ID NO:7 and SEQ ID NO:8.

Step 7. Cut plasmid from Step 6 with NotI and ligate with product obtained by PCR of the rev responsive element in the HXB2D plasmid (AIDS Repository) with primers SEQ ID NO:9 and SEQ ID NO:10.

Steps 6 and 7 are optional.

Example 8

The following construction, referred to herein as pENV, is useful to express HIV env genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pENV include a sequence that encodes vpu; a sequence that encodes rev; a sequence that encodes gp160; a sequence that encodes 50% of nef; a sequence that encodes vif; and, a sequence that encodes vpr with a 13 amino acid carboxy-end deletion. The vpu, rev, gp160 and nef sequences are derived from HIV-1 strain MN. The vif and vpr sequences are derived from HIV-1 strain HXB2.

Several safety features are included in pGAGPOL.rev. These include use of the CMV promoter and a non-retroviral poly(A) site. Furthermore, tat has been deleted and a 50S deletion of nef yields an "inactive" nef product. In addition, vif and vpr are placed out of normal sequence and a partial deletion of vpr further ensures an inactive vpr product.

Plasmid pENV is constructed as follows.

Step 1. Start with pUC18 digested with HindIII and EcoRI. The resulting fragment that contains the ColE1 origin of replication and the laci gene should be ligated with the EcoRI/HindIII fragment from pMAMneoBlue that contains the our sarcoma virus enhancer. The resulting plasmid or pMAMneo-Blue from Clontech (Palo Alto, Calif.) can then be digested with HindIII and BglII. Using standard techniques, ligate with fragment containing kan gene obtained by PCR of geneblock plasmid (Pharmacia).

Step 2. If pMAMneo-Blue used as starting plasmid, digest with MluI and EcoRI, fill in the ends with Klenow fragment of Polymerase I and religate.

Step 3. Them, with either pMAMneo-Blue or pUC18-derived plasmid, digest with HindIII and ligate with the SV40 polyA site and early splicing region obtained by PCR of pCEP4 (Invitrogen, San Diego Calif.) with primers SEQ ID NO:11 and SEQ ID NO:12.

Step 4a. Digest with BamHI and ligate with the CMV promoter obtained by PCR of pCEP4 (Invitrogen, San Diego Calif.) with primers SEQ ID NO:13 and SEQ ID NO:14.

Step 4b. Digest with BamHI and ligate with the MOMLV LTR obtained by PCR with primers SEQ ID NO:15 and SEQ ID NO:16.

Step 5. Digest with NotI and MluI and ligate with GP160 coding region obtained by PCR of pMN-ST1 with primers SEQ ID NO:17 and SEQ ID NO:18.

Step 6. Digest with MluI and ligate with sequences that encode vif in its entirety and vpr with a 13aa carboxy-end deletion by CPR of HXB2D plasmid (AIDS Repository) with primers SEQ ID NO:19 and SEQ ID NO:20.

Example 9

In some embodiments, the present invention relates to a method of immunizing an individual against HIV by administering a single inoculant. This inoculant includes a genetic construct that comprises at least one, preferably two, more preferably more than two or a plurality of the genes of the HIV virus or all of the structural genes. However, the inoculant does not contain a complete complement of all HIV genes. If a single cell is provided with a complete complement of viral genes, it is possible that a complete infectious virus can be assembled within the cell. Accordingly, a genetic construct according to the present invention is not provided with such a full complement of genes. As a safety precaution, one or more essential genes can be deleted or intentionally altered to further ensure that an infectious viral particle cannot be formed.

In some embodiments of the present invention, at least portions of one, two or all HIV structural genes are provided. The structural genes of HIV consist of gag, pol and env. Portions of at least one of these three genes are provided on a genetic construct. Accordingly, in some embodiments, at least a portion of each of gag and pol are provided on a genetic construct; in some embodiments, at least a portion of env is provided on a genetic construct; in some embodiments, at least a portion of gag is provided on a genetic construct; in some embodiments at least a portion of each of pol and env are provided on a genetic construct; in some embodiments, at least a portion of each of gag and env are provided on a genetic construct; in some embodiments at least a portion of pol is provided on a genetic construct. Optionally, the entire gene is provided. Optionally, in any of these constructs, HIV regulatory genes may also be present. The HIV regulatory genes are: vpr, vif, vpu, nef, tat and rev.

Example 10

As used herein, the term "expression unit" is meant to refer to a nucleic acid sequence which comprises a promoter operably linked to a coding sequence operably linked to a polyadenylation signal. The coding sequence may encode one or more proteins or fragments thereof. In preferred embodiments, a expression unit is within a plasmid.

As used herein, the term "HIV expression unit" is meant to refer to a nucleic acid sequence which comprises a promoter operably linked to a coding sequence operably linked to a polyadenylation signal in which the coding sequence encodes a peptide that comprises an epitope that is identical or substantially similar to an epitope found on an HIV protein. "Substantially similar epitope" is meant to refer to an epitope that has a structure which is not identical to an epitope of an HIV protein but nonetheless invokes an cellular or humoral immune response which cross reacts to an HIV protein. In preferred embodiments, the HIV expression unit comprises a coding sequence which encodes one or more HIV proteins or fragments thereof. In preferred embodiments, an HIV expression unit is within a plasmid.

In some embodiments of the present invention, a single genetic construct is provided that has a single HIV expression unit which contains DNA sequences that encode one or more HIV proteins or fragments thereof. As used herein, the term "single HIV expression unit construct" is meant to refer to a single genetic construct that contains a single HIV expression unit. In preferred embodiments, a single HIV expression unit construct is in the form of a plasmid.

In some embodiments of the present invention, a single genetic construct is provided that has more than one HIV expression units in which each contain DNA sequences that encode one or more HIV proteins or fragments thereof. As used herein, the term "multiple HIV expression unit genetic construct" is meant to refer to a single plasmid that contains more than one HIV expression units. In preferred embodiments, a multiple HIV expression unit construct is in the form of a plasmid.

In some embodiments of the present invention, a single genetic construct is provided that has two HIV expression units in which each contain DNA sequences that encode one or more HIV proteins or fragments thereof. As used herein, the term "two HIV expression unit genetic construct" is meant to refer to a single plasmid that contains two HIV expression units, i.e a multiple HIV expression unit genetic construct that contains two HIV expression unit genetic expression units. In a two HIV expression unit genetic construct, it is preferred that one HIV expression unit operates in the opposite direction of the other HIV expression unit. In preferred embodiments, a two HIV expression unit construct is in the form of a plasmid.

In some embodiments of the present invention, an HIV genetic vaccine is provided which contains a single genetic construct. The single genetic construct may be a single HIV expression unit genetic construct, a two HIV expression unit genetic construct or a multiple HIV expression unit genetic construct which contains more than two HIV expression units.

It is preferred that the genetic constructs of the present invention do not contain certain HIV sequences, particularly, those which play a role in the HIV genome integrating into the chromosomal material of the cell into which it is introduced. It is preferred that the genetic constructs of the present invention do not contain LTRs from HIV. Similarly, it is preferred that the genetic constructs of the present invention do not contain a psi site from HIV. Further, it is preferred that the reverse transcriptase gene is deleted and the integrase gene is deleted. Deletions include deletion of only some of the codons or replacing some of the codons in order to essentially delete the gene. For example, the initiation codon may be deleted or changed or shifted out of frame to result in a nucleotide sequence that encodes an incomplete and non-functioning.

It is also preferred that the genetic constructs of the present invention do not contain a transcribable tat gene from HIV. The tat gene, which overlaps the rev gene may be completely deleted by substituting the codons that encode rev with other codons that encode the same amino acid for rev but which does not encode the required tat amino acid in the reading frame in which tat is encoded. Alternatively, only some of the codons are switched to either change, i.e. essentially delete, the initiation codon for tat and/or change, i.e. essentially delete, sufficient codons to result in a nucleotide sequence that encodes an incomplete and non-functioning tat.

It is preferred that a genetic construct comprises coding sequences that encode peptides which have at least an epitope identical to or substantially similar to an epitope from HIV gag, pol, env or rev proteins. It is more preferred that a genetic construct comprises coding-sequences that encode at least one of HIV gag, pol, env or rev proteins or fragments thereof. It is preferred that a genetic construct comprises coding sequences that encode peptides which have more than one epitopes identical to or substantially similar to an epitope from HIV gag, pol, env or rev proteins. It is more preferred that a genetic construct comprises coding sequences that encode more than one of HIV gag, pol, env or rev proteins or fragments thereof.

In some embodiments, a genetic construct comprises coding sequences that encode peptides which have at least an epitope identical to or substantially similar to an epitope from HIV vif, vpr, vpu or nef proteins. In some embodiments, a genetic construct comprises coding sequences that encode at least one of HIV vif, vpr, vpu or nef proteins or fragments thereof.

A single HIV expression unit genetic construct may comprise coding regions for one or more peptides which share at least one epitope with an HIV protein or fragment thereof in a single expression unit under the regulatory control of single promoter and polyadenylation signal. It is preferred that genetic constructs encode more than one HIV protein or fragment thereof. The promoter may be any promoter functional in a human cell. It is preferred that the promoter is an SV40 promoter or a CMV promoter, preferably a CMV immediate early promoter. The polyadenylation signal may be any polyadenylation signal functional in a human cell. It is preferred that the polyadenylation signal is an SV40 polyadenylation signal, preferably the SV40 minor polyadenylation signal. If more than one coding region is provided in a single expression unit, they may be immediately adjacent to each other or separated by non-coding regions. In order to be properly expressed, a coding region must have an initiation codon and a termination codon.

A two HIV expression unit genetic construct may comprise coding regions for one or more peptides which share at least one epitope with an HIV protein or fragment thereof on each of the two expression units. Each expression unit is under the regulatory control of single promoter and polyadenylation signal. In some embodiments, it is preferred that genetic constructs encode more than one HIV protein or fragment thereof. In some embodiments, it is preferred that nucleotide sequences encoding gag and pol are present on one expression unit and nucleotide sequences encoding env and rev are present on the other. The promoter may be any promoter functional in a human cell. It is preferred that the promoter is an SV40 promoter or a CMV promoter, preferably a immediate early CMV promoter. The polyadenylation signal may be any polyadenylation signal functional in a human cell. It is preferred that the polyadenylation signal is an SV40 polyadenylation signal, preferably the SV40 minor polyadenylation signal. If more than one coding region is provided in a expression unit, they may be immediately adjacent to each other or separated by non-coding regions. In order to be properly expressed, a coding region must have an initiation codon and a termination codon.

According to some embodiments of the present invention, the MHC Class II crossreactive epitope in env is deleted and replaced with the analogous region from HIV II.

When a genetic construct contains gag and/or pol, it is generally important that rev is also present. In addition to rev, a rev response element may be provided with gag and pol for increased expression of those genes.

When genetic constructs are produced that it is preferred that the env gene used in plasmid 1 is derived from MN or MN-like isolates including clinical isolates resembling MN, preferably non-syncytial inducing clinical isolates, preferably those that are macrophage tropic from early stage clinical isolates.

Multiple proteins may be produced from a single expression unit by alternative splicing. Splicing signals are provided to allow alternative splicing which produces different messages encoding different proteins.

Example 11

FIG. 1 shows four backbones, A, B, C and D. FIG. 2 shows 4 inserts, 1, 2, 3 and 4. Insert 1 supports expression of gag and pol; the rev response element was cloned in a manner to conserve the HIV splice acceptor. Insert 2 is similar to insert 1 as it too supports expression of gag and pol except the rev response element was cloned without conserving the HIV splice acceptor Insert 3 supports expression of gag and pol, includes a deletion of the integrase gene and does not include the presence of the cis acting rev response element. Insert 4 supports expression of rev, vpu and env. The env may have the MHC class II cross reactive epitope altered to eliminate crossreactivity and the V3 loop may be altered to eliminate the possibility of syncytia formation.

In some embodiments, backbone A is used with insert 1. Such constructs optionally contain the SV40 origin of replication. Plasmid pAlori+ is backbone A with insert 1 and the SV40 origin of replication. Plasmid pAlori− is backbone A with insert 1 without the SV40 origin of replication. Additionally, either pAlori+ or pAlori− may include integrase yielding pAlori+int+ and pAlori−int+, respectively. Plasmids pAlori+, pAlori−, pAlori+int+ and pAlori−int+ may be further modified by functionally deleing the reverse transcriptase (RT) gene yielding pAlori+RT−, pAlori−RT−, pAlori+int+RT− and pAlori−int+RT−, respectively.

In some embodiments, backbone A is used with insert 2. Such constructs optionally the SV40 origin of replication. Plasmid pA2ori+ is backbone A with insert 2 and the SV40 origin of replication. Plasmid pA2ori− is backbone A with insert 1 without the SV40 origin of replication. Additionally, either pA2ori+ or pA2ori− may include integrase yielding pA2ori+int+ and pA2ori−int+, respectively. Plasmids pA2ori+, pA2ori−, pA2ori+int+ and pA2ori−int+ may be further modified by functionally deleing the reverse transcriptase (RT) gene yielding pA2ori+RT−, pA2ori−RT−, pA2ori+int+RT− and pA2ori−int+RT−, respectively.

In some embodiments, backbone B is used with insert 1. Such constructs optionally the SV40 origin of replication. Plasmid pBlori+ is backbone B with insert 1 and the SV40 origin of replication. Plasmid pBlori– is backbone B with insert 1 without the SV40 origin of replication. Additionally, either pBlori+ or pBlori– may include integrase yielding pBlori+int+ and pBlori–int+, respectively. Plasmids pBlori+, pBlori–, pBlori+int+ and pBlori–int+ may be further modified by functionally deleting the reverse transcriptase (RT) gene yielding pBlori+RT–, pBlori–RT–, pBlori+int+RT– and pBlori–int+RT–, respectively.

In some embodiments, backbone B is used with insert 2. Such constructs optionally the SV40 origin of replication. Plasmid pB2ori+ is backbone B with insert 2 and the SV40 origin of replication. Plasmid pB2ori– is backbone B with insert 1 without the SV40 origin of replication. Additionally, either pB2ori+ or pB2ori– may include integrase yielding pB2ori+int+and–pB2ori–int+, respectively. Plasmids pB2ori+, pB2ori–, pB2ori+int+ and pB2ori–int+ may be further modified by functionally deleing the reverse transcriptase (RT) gene yielding pB2ori+RT–, pB2ori–RT–, pB2ori+int+RT– and pB2ori–int+RT–, respectively.

In some embodiments, backbone A minus rev is used with insert 3. Such constructs optionally the SV40 origin of replication. Plasmid pA/r–3ori+ is backbone A with insert 2 and the SV40 origin of replication. Plasmid pA/r–3ori– is backbone A minus rev with insert 3 without the SV40 origin of replication. Additionally, either pA/r–3ori+ or pA/r–3 ori–may include integrase yielding pA/r–3ori+int+ and pA/r–3ori–int+, respectively. Plasmids pA/r–3ori+, pA/r–3ori–, pA/r–3ori+int+ and pA/r–3ori–int+ may be further modified by functionally deleing the reverse transcriptase (RT) gene yielding pA/r–3ori+RT–, pA/r–3ori–RT–, pA/r–3ori+int+RT– and pA/r–3ori–int+RT–, respectively.

In some embodiments, backbone C is used with insert 1. Such constructs optionally the SV40 origin of replication. Plasmid pC1ori+ is backbone C with insert 1 and the SV40 origin of replication. Plasmid pC1ori– is backbone C with insert 1 without the SV40 origin of replication. Additionally, either pC1ori+ or pC1ori– may include integrase yielding pC1ori+int+ and pC1ori–int+, respectively. Plasmids pC1ori+, pC1ori–, pC1ori+int+ and pC1ori–int+ may be further modified by functionally deleing the reverse transcriptase (RT) gene yielding pC1ori+RT–, pC1ori–RT–, pC1ori+int+RT– and pC1ori–int+RT–, respectively.

In some embodiments, backbone C is used with insert 2. Such constructs optionally the SV40 origin of replication. Plasmid pC2ori+ is backbone C with insert 2 and the SV40 origin of replication. Plasmid pC2ori– is backbone C with insert 2 without the SV40 origin of replication. Additionally, either pC2ori+ or pC2ori– may include integrase yielding pC2ori+int+ and pC2ori–int+, respectively. Plasmids pC2ori+, pC2ori–, pC2ori+int+ and pC2ori–int+ may be further modified by functionally deleing the reverse transcriptase (RT) gene yielding pC2ori+RT–, pC2ori–RT–, pC2ori+int+RT– and pC2ori–int+RT–, respectively.

In some embodiments, backbone C is used with insert 3. Such constructs optionally the SV40 origin of replication. Plasmid pC3ori+ is backbone C with insert 3 and the SV40 origin of replication. Plasmid pC3ori– is backbone C with insert 3 without the SV40 origin of replication. Additionally, either pC3ori+ or pC3ori– may include integrase yielding pC3ori+int+ and pC3ori–int+, respectively. Plasmids pC3ori+, pC3ori–, pC3ori+int+ and pC3ori–int+ may be further modified by functionally deleing the reverse transcriptase (RT) gene yielding pC3ori+RT–, pC3ori–RT–, pC3ori+int+RT– and pC3ori–int+RT–, respectively.

In some embodiments, backbone D is used with insert 4. Such constructs optionally the SV40 origin of replication. Plasmid pD4ori+ is backbone D with insert 4 and the SV40 origin of replication. Plasmid pD4ori– is backbone D with insert 4 without the SV40 origin of replication.

Example 12

In some embodiments, a single expression unit/single inoculant genetic vaccine is provided which comprises a genetic construct that includes a coding sequence which encodes a peptide that has at least one epitope which is an identical to or substantially similar to epitopes of HIV proteins. The coding sequence is under the regulatory control of the CMV immediate early promoter and the SV40 minor polyadenylation signal.

In some embodiments, a single expression unit/single inoculant genetic vaccine is provided which comprises a genetic construct that includes a coding sequence which encodes at least one HIV protein or a fragment thereof. The coding sequence is under the regulatory control of the CMV immediate early promoter and the SV40 minor polyadenylation signal. The HIV protein is selected from the group consisting of gag, pol, env and rev. In some embodiments it is preferred that the genetic vaccine is provided which comprises a genetic construct that includes a coding sequence which encodes at least two HIV proteins or a fragments thereof selected from the group consisting of gag, pol, env and rev or fragments thereof. In some embodiments, it is preferred that the genetic vaccine is provided which comprises a genetic construct that includes a coding sequence which encodes at least three HIV proteins or a fragments thereof selected from the group consisting of gag, pol, env and rev or fragments thereof. In some embodiments, it is preferred that the genetic vaccine is provided which comprises a genetic construct that includes a coding sequence which encodes gag, pol, env and rev or fragments thereof.

In some embodiments, a dual expression unit/single inoculant genetic vaccine is provided which comprises a genetic construct that includes two expression units each of which comprises a coding sequence which encodes a peptide that has at least one epitope which is an identical to or substantially similar to epitopes of HIV proteins. The coding sequence is under the regulatory control of the CMV immediate early promoter and the SV40 minor polyadenylation signal. The two expression units are encoded in opposite directions of each other.

In some embodiments, a dual expression unit/single inoculant genetic vaccine is provided which comprises a genetic construct that includes two expression units each of which comprises a coding sequence which encodes at least one HIV protein or a fragment thereof. Each expression unit comprises a coding sequence that is under the regulatory control of the CMV immediate early promoter and the SV40 minor polyadenylation signal. The HIV protein is selected from the group consisting of gag, pol, env and rev. In some embodiments it is preferred that the genetic vaccine is provided which comprises a genetic construct that includes two expression units, at least one of which comprises a coding which encodes at least two HIV proteins or a fragments thereof selected from the group consisting of gag, pol, env and rev or fragments thereof and the other comprises at least one HIV proteins or a fragments thereof selected from the group consisting of gag, pol, env and rev or fragments thereof. In some embodiments, it is preferred that the genetic vaccine is provided which comprises a genetic construct that includes two expression units, at least one of which comprises a coding sequence which encodes at least three HIV proteins or a fragments thereof selected from the group consisting of gag, pol, env and rev or fragments thereof and the other comprises at least one HIV proteins or a fragments thereof selected from the group consisting of gag, pol, env and rev or fragments thereof. In some embodiments, it is preferred that the genetic vaccine is provided which comprises a genetic construct that comprises two expression units and includes a coding sequence which encodes gag, pol, env and rev or fragments thereof.

Example 13

A genetic construct, plasmid pCMN160Δ16 was made for use in an anti-HIV pharmaceutical kit or pharmaceutical composition. pCMN160Δ16 was constructed as follows:

Step 1: Primers SEQ ID NO:23 and SEQ ID NO:22 were used a PCR fragment from HIV/MN genomic DNA.

Step 2: Primers SEQ ID NO:21 and SEQ ID NO:24 were, used a PCR fragment from HIV/MN genomic DNA.

Step 3: Primers SEQ ID NO:23 and SEQ ID NO:24 were combined with 2 μl of reaction material from Steps 1 and 2.

Step 4: Reaction product from Step 3 was cut with Not1 and Mlu1 and inserted into Backbone A described in Example 11 cut with Not1 and Mlu1.

Plasmid pCMN160Δ16 is thereby formed which contains as an insert to Backbone A a coding region which encodes the MN strain ENV Protein with the rev region and half of nef having HLA-DB region changes to HIV-2.

Example 14

The plasmid pGAGPOL.rev2 was made as follows. First the backbone was made. Then an insert with HIV gag and pol was generated and inserted into the backbone.

The backbone was prepared as follows.

Step 1. Digest pMAMneo (Clonetech) with Bgl1. Fill-in with Klenow fragment of Polymerase I. Cut with HindIII. Gel purify 1763 bp fragment.

Step 2. Amplify $Kan^R$ gene from plasmid pJ4Ωkan$^+$ (Kanmycin resistance gene obtained from Pharmacia Inc. cloned into pJ4Ω obtained as a gift from the Imperial Cancer Research Fund UK; pJ4Ω was originally constructed and reported by Morgenstern, J. P. and H. Land, *Nucl. Acids Res.* 18(4):1068, which is incorporated herein by reference, with oligos SEQ ID NO:25 and SEQ ID NO:26. Blunt off PCR product. Cut with HindIII. Gel purify PCR fragment.

Step 3. Ligate the vector backbone generated from pMAMneo and described in step #1 with the PCR product encoding the $Kan^R$ gene and described in step #2. Isolate plasmid containing the $Kan^R$ gene and the bacterial origin of replication.

Step 4. Digest resulting plasmid with MluI, fill-in with Klenow fragment of DNA polymerase I. Ligate with SacII linker (New England Biolabs).

Step 5. Digest plasmid obtained in step 4 with AseI and SspI.

Step 6. PCR part of the $Kan^R$ gene from the plasmid described in step 3 using primers SEQ ID NO:27 and SEQ ID NO:28. Cut PCR product with SspI and AseI.

Step 7. Ligate largest fragment obtained in step 5 with PCR product obtained in step 6.

Step 8. Cut ligation product/plasmid obtained in step 7 with HindIII. Blunt off with the Klenow fragment of DNA polymerase I.

Step 9. Cut pCEP4 (Invitrogen) with SalI to release a DNA fragment containing the CMV promoter, polylinker, and SV40 poly A site. Purify this fragment and blunt-off with the Klenow fragment of DNA Polymerase I.

Step 10. Ligate the plasmid obtained in step 8 and the fragment obtained in step 9. Isolate plasmid containing the bacterial origin of replication, the $Kan^R$ gene, the RSV enhancer, the CMV promoter, polylinker, and the SV40 poly A site.

Step 11. Cut plasmid obtained in step 10 with BamHI and NheI.

Step 12. Anneal oligonucleotides SEQ ID NO:29 and SEQ ID NO:30.

Step 13. Ligate the plasmid obtained in step 10 with the annealed oligonucleotides obtained in step 12. Isolate plasmid containing the adapter contained in step 12.

Step 14. Digest plasmid obtained in step 13 with SalI and MluI.

Step 15. PCR amplify the rev open reading frame using BBG35 (RD Systems Inc. Minneapolis, Minn.; which contains the coding region for rev from HIV strain HX3B in pUC19) as a template and primers SEQ ID NO:31 and SEQ ID NO:32. Digest the PCR product with SalI and MluI.

Step 16. Ligate the plasmid obtained in step 14 with the PCR product produced in step 15. Isolate plasmid containing the rev coding region.

Preparation of gag/pol insert.

Step 1. A subclone of part of the HIV-I (HXB2) genome that was cloned into Bluescript (Stratagene). The subclone of HIV-1 contains the complete 5'LTR and the rest of the HIV-1 genome to nucleotide 5795 (Genbank numbering) cloned into the XbaI and SalI sites of Bluescript. The HIV-1 sequences are obtained from the HXB2D plasmid (AIDS Repository).

Step 2. PCR part of the gag coding region from the open reading frame of the plasmid described in step 1 (the subclone of part of the HIV-1 HXB2 genome that is cloned into Bluescript) using primers SEQ ID NO:33 and SEQ ID NO:34:

Step 3. Digest plasmid described in step 1 (the subclone of part of the HIV-1 HXB2 genome that is cloned into Bluescript) with EcoRI. Purify the plasmid that contains the pBluescript backbone, the 5' HIV-1 LTR, the gag coding region and part of the pol coding region and religate.

Step 4. Cut the plasmid obtained in step 3 with NotI and SpeI and ligate with the PCR fragment described in Step 2 after it is digested with Notl and SpeI. Isolate plasmid that contain the PCR fragment instead of the original NotI/SpeI fragment which contains the 5' HIV-1 LTR.

Step 5. Digest the plasmid obtained in step 4 with EcoR1 and SalI.

Step 6. Anneal oligonucleotides SEQ ID NO:35 and SEQ ID NO:36.

Step 7. Ligate the plasmid obtained in step 5 with the adapter obtained in step 6. Isolate plasmid containing the adapter cloned into the EcoRI/SalI sites.

Step 8. Digest the plasmid obtained in step 7 with NdeI and EcoRI.

Step 9. PCR amplify the Rev Response Element (RRE) from a plasmid containing the RRE sequence from HIV-1 strain HXB2 using primers SEQ ID NO:37 and SEQ ID NO:38. Digest the PCR product with NdeI and EcoRI.

Step 10. Ligate the plasmid obtained in step 8 with the PCR product obtained in step 9. Isolate plasmid containing the insert with the RRE sequence.

Step 11. Digest the plasmid obtained in step 10 with NotI and SalI and isolate the fragment containing the gag coding region, the modified pol coding region, and the RRE sequence.

Step 12. Digest the plasmid obtained in step 16 of the protocol for preparing the backbone which is described above with NotI and SalI.

Step 13. Ligate the plasmid obtained in step 12 with the insert obtained in step 11. Isolate plasmids that contain the insert containing the gag coding region, the modified pol coding region, and the RRE sequence.

Step 14. Digest plasmid obtained in step 13 with XbaI and NheI, Blunt-off ends and religate. Isolate the plasmid that is lacking the KpnI site that is present between the XbaI and NheI sites in the plasmid obtained in step 13.

Step 15. Digest the plasmid obtained in step 14 with KpnI and isolate the largest fragment.

Step 16. Anneal oligonucelotides SEQ ID NO:39 and SEQ ID NO:40.

Step 17. Ligate the purified plasmid fragment obtained in step 15 with the adapter obtained in step 16. Isolate plasmid containing the adapter inserted at the KpnI site of the plasmid obtained in step 15.

Example 15

Genetic Immunization with Genes for Regulatory Proteins

Part of the difficulty of combatting HIV arises from the extraordinary variability of the virus and its ability to quickly mutate into new forms. Not only is there substantial protein sequence variation among HIV isolates found in the human population as a whole, but the virus mutates so quickly that every HIV-infected individual actually harbors a number of related HIV microvariants. Such HIV isolates exhibit differences in replication efficiency, tropism, susceptibility to neutralization, and drug resistance. As drug-resistant mutants appear, the benefits of drug therapy fade. With AZT, drug resistance typically arises within the first year of therapy. This constant generation of escape mutants may play a part in the ability of HIV to finally overwhelm host defenses after a long period in which the virus appears to be held in check.

This mutational drift has been reported in various regions of the gp120 envelope glycoprotein, including the principal neutralizing domain of the V3 loop, and in the HIV core proteins as well. HIV regulatory proteins are much more highly conserved than the structural proteins and also exhibit less mutational drift over time. Regulatory proteins therefore present attractive targets for antiviral attack.

HIV exhibits a remarkable temporal regulation of expression of regulatory vs structural proteins. In the early phase of viral replication, mRNAs encoding the regulatory proteins Tat, Rev and Nef predominate, whereas in the late phase, there is greater expression of mRNAs encoding structural proteins, including Gag, Pol, and Env precursors, and many accessory proteins. This shift from early to late phase is triggered when the Rev protein reaches a particular level. The predominance of Tat, Rev and Nef early in the viral replication cycle also makes these proteins favorable targets for antiviral attack. This is especially true for tat and rev, which play absolutely essential roles in transcriptional and post-translational regulation of HIV gene expression, and predominate early in the viral replication cycle, before transcription of viral structural proteins and production of infectious viral particles.

In contrast to tat and rev, which clearly play essential roles in HIV replication, other regulatory proteins such as nef, vpr, vif, and vpu are sometimes referred to as "accessory" proteins. Their functions are less well understood, and the degree to which viral replication is attenuated by loss of a particular function varies considerably and may depend on the host cell being infected. Nevertheless, the strong conservation of such functions among widely diverse HIV isolates, as well as other primate immunodeficiency viruses, suggests the importance of these "accessory" functions in the natural infection process. (See in general, Terwilliger, E. F., (1992) *AIDS Research Reviews* 2:3–27, W. C. Koff, F. Wong-Staal, and R. C. Kennedy, eds. (New York:Marcel Dekker, Inc.). In fact, primate recombinant viruses deleted in either vpr, nef or vif are non-pathogenic in vivo, further demonstrating the importance of these accessory genes in the life cycle of the virus.

There is some evidence that higher level, more protective immune responses against HIV could be achieved by presenting a select few regulatory and/or enzymatic proteins, rather than the entire complement of HIV genes. Accordingly, a focused immunization strategy may desirably involve genetic immunization using coding sequences for one or more regulatory, non-structural HIV proteins, including tat, rev, vpr, nef, vpu or vif. Only vpr has been found to be associated with viral particles, whereas other regulatory proteins, including tat, rev, nef, vif and vpu, are not virion associated.

In some embodiments of genetic immunization against HIV using regulatory genes, the one or more of tat, rev, nef, vif and vpu genes are inserted into backbone A which is described in Example 11. It is preferred that tat and/or rev is used. In some embodiments, tat or rev are inserted into backbone A which is described in Example 11. In some embodiments, Next in descending order of desirability as targets are nef, vpr, vif, and vpu. Preferably, more than one regulatory gene will be employed, including tat and rev; tat, rev, and nef; tat, rev, nef, and vpr; tat, rev, nef, vpr, and vif; tat, rev, nef, vpr, vif, and vpu; as well as combinations thereof; and, optionally, such additional regulatory genes as tev.

The Tat protein is a transactivator of LTR-directed gene expression. It is absolutely essential for HIV replication. Tat is produced early in the viral replication cycle and functional Tat is required for expression of Gag, Pol, Env and Vpr. The predominant form of Tat is an 86-amino acid protein derived from two exon mRNAs. The amino-terminal 58 amino acids are sufficient for transactivation, although with reduced activity. Tat acts on a cis-acting sequence termed tar, to produce a dramatic increase in LTR-driven gene expression. Tat may act in part through increased RNA synthesis and in part by increasing the amount of protein synthesized per RNA transcript. Until recently, Tat was thought to act only on the HIV-1 LTR. However, Tat-activated expression from the JC virus late promoter has also been reported. Tat may also stimulate cell proliferation as an exogenous factor, and may play a contributory role in promoting the growth of Kaposi's Sarcoma in HIV-infected individuals. Because of such potentially detrimental effects in both HIV-infected and -noninfected individuals, preferred tat constructs employed for genetic immunization are modified to express only non-functional Tat. Mutations capable of inactivating Tat or Rev can in addition act as transdominant mutations, thereby potentially inactivating any functional Tat being produced in an HIV-infected individual.

Rev is a second regulatory protein of HIV that is essential for viral replication. It is a 19 kD (116 amino acid) protein which is expressed from two coding exons found in a variety of multiply spliced mRNAs. Two distinct domains have been identified, a basic region involved in binding to RRE (Rev-response-element)containing transcripts and an "activation" domain that induces nuclear exports of such transcripts as a result of binding. In the course of natural viral infection, Rev is required for expression of the HIV structural proteins Gag, Pol, and Env, as well as Vpr.

Vpr is a 15 kD protein (96 amino acids) in most HIV-1 strains, although the Vpr open reading frame is extensively truncated in many viral strains extensively passaged in cell culture. The vpr open reading frame is also present in HIV-2 and most SIV isolates. Vpr is the first retroviral regulatory protein found to be associated with HIV viral particles. Its presence in the HIV virion suggests it may serve a function at some early point in the viral replication cycle. Vpr accelerates HIV replication, especially early in infection. Vpr increases the level of expression of reporter genes linked to the HIV LTR by about three fold. Moreover, Vpr and Tat appear to act synergistically with respect to LTR-linked genes. vpr can be isolated from the serum of HIV-infected individuals and appears to increase the ability of the virus to infect new cells. Vpr has also been found to inhibit cell proliferations and to induce cell differentiation (Levy, D. N. et al., *Cell* (1993) 72:1–20), a finding that may be significant in view of reports that primary monocyte/macrophages are infectible in vitro only while undergoing differentiation (Schuitemaker, H. et al., (1992) *J. Clin. Invest.* 89:1154–1160. Even cells that are unable to support HIV replication may be disregulated by the effects of Vpr. For example, Vpr may be responsible for the muscle wasting frequently observed in AIDS patients. Because of the potentially detrimental activity of Vpr, genetic immunization should preferably be carried out with a modified vpr construct which will express a non-functional Vpr protein.

Nef (also called 3' orf in older literature) is a 25–27 kD protein. It has been suggested that Nef may be involved in the downregulation of CD4+ T lymphocytes. In addition, Nef may play a role in cell signaling. Nef appears to be important for the establishment of HIV infection in vivo. Nef-specific CTLs are believed to be important in controlling HIV infection in vivo.

Vif is a 23 kD cytoplasmic protein designated "viral infectivity factor". Although Vif-defective mutant viruses are not compromised with respect to cell-to-cell transmission, they exhibit a profound decrease in ability to infect many CD4+ cell lines. Without Vif, there is decreased budding of virus, and decreased infectivity. In primate studies, Vif deletion mutants exhibit a severely diminished ability to establish infection in vivo. These studies support a clinical role for Vif in virus replication in the host.

Vpu is a 15–20 kD (81 amino acid) protein. Although Vpu(+) and Vpu(−) viruses produce the same amount of viral protein, the latter exhibit increased intracellular accumulation of viral proteins together with decreased extracellular virus. This suggests that Vpu may be involved in the assembly and/or release of viral particles.

Simple retroviruses, such as murine and avian viruses, lack proteins analogous to the HIV-1, HIV-2, and SIV regulatory proteins. In such animals retroviral infection tends to be self-limiting, with clearance of virus and decreased pathogenicity. Similarly, HTLV-1, which includes only Tax (which acts much like Tat and also exhibits vpr-like activity) and Rex (which acts much like Rev) is cleared in many individuals. Genetic immunization with regulatory genes is considered relevant not only for HIV, but also for viruses such as HBV (X gene product) and HCV, and HTLV-1 (Tax) and (Rex). In all of these viruses the regulatory genes are believed to play a critical role in the virus life cycle and the establishment of infection.

Example 16

Construction of HIV-1 Regulatory Plasmid, pREG

The pREG plasmid is constructed in a stepwise fashion, and each intermediate can be tested for protein expression before construction is continued. An expression vector supporting the expression of tat and rev is constructed via two steps. First, an amplification product containing a 5' NheI site, the HIV-1 major splice donor site, the majority of the tat coding region, the region encoding the amino terminal region of the rev protein and an AvaII site is amplified from a synthetic template. This synthetic template is generated using the published sequences of HXB2 strain of HIV-1 obtained from the GenBank Database, and is altered to mutate the cysteine residues at positions 22 and 30 of the tat protein. These mutations have been shown to render tat non-functional (Kuppuswamy, et al. (1989) *Nucleic Acids Research* 17(9): 3551–3561).

The PCR product is ligated into a vector that is digested with NheI and AvaII and which contains a kanamycin resistance gene and a pBR322 origin of replication. In addition, this plasmid contains a cytomegalovirus promoter, a Rous sarcoma virus enhancer, the rev coding region and a SV40 polyadenylation signal. The rev sequence present in the plasmid is derived from the proviral clone of HIV-1 III$_B$. This will generate an expression vector containing a complete, but mutated, tat coding region and a complete rev coding region.

The subsequent step is performed to generate a PCR product containing an AvaII site at its 5' end, a mutation at amino acid position 81 of rev, approximately 30% of the rev coding region, approximately 30% of the nef coding region, and a MluI site at the 3' end. The amino acid change at position 81 has been shown to eliminate rev function, and therefore, the resulting plasmid will lead to production of non-functional rev protein (Bogard, H. and Greene, W. C. (1993) *J. Virol.* 67(5):2496–2502). It is assumed that the major deletion of the nef coding region will result in production of a non-functional nef protein. The 5' AvaII site and the mutation at amino acid position 81 of the rev protein are introduced on the 5' PCR primer which is complementary to the coding region of rev containing both the AvaII site and the nucleotide encoding amino acid 81. A stop codon causing termination of Nef at amino acid position 63 and the 3' coding cloning site, MluI, will be introduced by the 3' PCR primer. The template for this PCR amplification is a plasmid or synthetic template containing the rev and nef coding regions from the MN strain of HIV-1. The resulting PCR product will be digested with AvaII and MluI, and used to replace the smaller AvaII-MluI fragment which results after digestion of the tat-rev plasmid described in the preceding paragraph with AvaII and MluI.

Optionally, vpr can be added to this plasmid in one of two sites. In one approach, vpr can be amplified using a 5' PCR primer containing MluI site upstream of sequences which span the vpr translational start codon and a 3' PCR primer complementary to the vpr stop codon and sequences that flank it which also contain a MluI cloning site. Sequences upstream of the start codon contain a splice acceptor. The PCR product can be digested with MluI and inserted into the tat rev nef plasmid described above after its digestion with MluI.

Alternatively, the vpr amplification can be performed in analogous manner, however, the PCR primers would contain restriction sites compatible with cloning into another vector so that it is expressed under the control of a second eukaryotic promoter. The cassette derived from this plasmid, containing the second promoter followed by the vpr coding region, followed by the a polyA sequence, could be released by digestion with restriction enzymes that flank the cassette, but do not cut within it. The resulting DNA fragment would be cloned into a unique site of the tat, rev, vpr plasmid that falls outside of the region necessary for the expression of tat rev vpr. In this way, a plasmid having two expression units is formed.

Example 17

Construction of HCV and HTLV-1 Plasmids

A similar approach can be used to generate a plasmid expressing HTLV-1 or HCV encoded proteins having enzymatic functions required for the viral life cycle and/or for the regulatory proteins of these viruses. For HTLV-1, a plasmid encoding the regulatory protein, TAX, is generated using the a plasmid backbone and a cloning strategy similar to those described above. Such HCV genes that encode enzymatic proteins include the RNA-dependent RNA-polymerase, a protein having helicase/protease function. The sequences necessary are published and available through GenBank. The viral organization of HTLV-1 and HCV are published in Cann, A. J. and Chen, I.S.Y. *Virology* 2nd Edition, edited by B. N. Fiddr, Raven Press, Ltd., New York, 1990 and Bradley, D. W. *Transfusion Medicine Reviews*, 1(2):93–102, 1992, respectively.

Example 18

Genetic Immunization with Enzymatic Genes

Genetic immunization with genes encoding proteins with enzymatic functions, such as the HIV pol gene can also be an important antiviral strategy since enzymes such as Pol are necessary for the production of live virus. Without polymerase or any of its component functions, HIV is non-pathogenic and non-infectious. Similarly, the enzymatic genes of other viruses, such as the HBV polymerase, are attractive targets for genetic immunization. See, e.g., Radziwill et al., Mutational Analysis of the Hepatitis B Virus P Gene Product: Domain Structure and RNase H Activity, *J. Virol.* 64 (2): 613–620 (1990).

One reason for the attractiveness of viral enzymes as an immunological target is the limited ability of such enzymes to mutate their amino acid sequence and still maintain their enzymatic functions. For example, with HIV-1, Pol exhibits a limited number of "escape" mutations that are associated with resistance to nucleotide analogs such as AZT. However, the vast majority of immunological targets within the protein are preserved even in the drug escape mutants.

Example 19

Construction of HBV Polymerase Plasmid

Experiments reported in the literature indicate that HBV polymerase expression has been achieved in tissue culture cells when both the core and polymerase open reading frames are present in a mRNA molecule. It has also been demonstrated that in this situation, mutation of the core ATG did not influence polymerase expression.

The HBV genome is amplified from a plasmid containing a head-to-tail dimer of the ADW HBV strain. Because expression of polymerase only, and not core is desired, the 5' PCR primer is designed to mutate the precore and core translation initiation codons. In addition, this primer also introduces a mutant DR1 sequence to eliminate the possibility of the generation of a replication-competent HBV genomic RNA. This PCR product is placed into a plasmid containing a kanamycin resistance gene and a pBR322 origin of replication. In addition, this plasmid contains a cytomegalovirus promoter, a Rous sarcoma virus enhancer, and a SV40 polyadenylation signal. The translation initiation codons for surface antigen and the product of the X coding region are mutated to prevent the expression of the HBS and X gene products.

According to another approach to achieve expression of the HBV polymerase, a PCR product encoding the entire polymerase coding region is amplified and cloned into a vector containing a kanamycin resistance gene and a pBR322 origin of replication. In addition, this plasmid contains a cytomegalovirus promoter, a Rous sarcoma virus enhancer, and a SV40 polyadenylation signal. The 5' PCR primer for this amplification contains a cloning site and spans the translational initiation codon of the polymerase gene. The 3' PCR product contains a restriction site for cloning the insert into the expression vector and also is complementary to the traditional stop codon of the HBV polymerase gene and sequences that flank this stop codon. After ligation of this PCR product into a plasmid containing the kanamycin resistance gene, a pBR322 origin of replication, a cytomegalovirus promoter, a Rous sarcoma virus enhancer, and a SV40 polyadenylation signal, the translation initiation codons for the Hepatitis B surface antigen and X genes are mutated to prevent expression of these gene products. An alternative strategy is used similar to that described above, however, the 3' PCR primer in this case includes the HBVpolyA signal and sequences which flank this signal. This 3' primer is used in the case that sequences including and/or surrounding the HBV polyA signal are important for expression. A mutational analysis has demonstrated that the function of the HBV polymerase gene product can be eliminated by particular nucleotide changes (Radziwell, G. et al. (1990) *J. Virol.* 64(2):613–620). Before utilizing a plasmid constructed as described above, the expressed polymerase can be mutated by the introduction of one of these mutations or others that are analogous.

Example 20

Gene constructs useful in pharmaceutical kits and compositions for vaccination against and treatment for HBV are constructed with vectors described as backbones in Example 11. The plasmids contain HBV structural genes, particularly genes that encode HBV surface antigen and/or HBV core antigen core and/or HBV precore antigen.

Example 21

Gene constructs useful in pharmaceutical kits and compositions for vaccination against and treatment for HCV are constructed with vectors described as backbones in Example 11. The plasmids contain HCV structural genes, particularly genes that encode HCV core protein and/or HCV envelope protein.

Example 22

The gene construct pREV was designed which contains a nucleotide sequence that encodes HIV rev as the sole target protein. The coding sequence of rev is cloned into Backbone A described in Example 11 from BBG35 (RD Systems Inc. Minneapolis, Minn.) which contains the coding region of rev from HIV strain HX3B in pUC19.

TABLE 1

| Picornavirus Family | |
|---|---|
| Genera: | Rhinoviruses: (Medical) responsible for ~50% cases of the common cold. Etheroviruses: (Medical) includes polioviruses, coxsackieviruses, echoviruses, and human enteroviruses such as hepatitis A virus. Apthoviruses: (Veterinary) these are the foot and mouth disease viruses. |
| Target antigens: | VP1, VP2, VP3, VP4, VPG |
| Calcivirus Family | |
| Genera: | Norwalk Group of Viruses: (Medical) these viruses are an important causative agent of epidemic gastroenteritis. |
| Togavirus Family | |
| Genera: | Alphaviruses: (Medical and Veterinary) examples include Senilis viruses, RossRiver virus and Eastern & Western Equine encephalitis. Reovirus: (Medical) Rubella virus. |
| Flariviridue Family | Examples include: (Medical) dengue, yellow fever, Japanese encephalitis, St. Louis encephalitis and tick borne encephalitis viruses. |
| Hepatitis C Virus: | (Medical) these viruses are not placed in a family yet but are believed to be either a togavirus or a flavivirus. Most similarity is with togavirus family. |
| Coronavirus Family: | (Medical and Veterinary) Infectious bronchitis virus (poultry) Porcine transmissible gastroenteric virus (pig) |

TABLE 1-continued

| | |
|---|---|
| | Porcine hemagglutinating encephalomyelitis virus (pig) Feline infectious peritonitis virus (cats) Feline enteric coronavirus (cat) Canine coronavirus (dog) The human respiratory coronaviruses cause ~40 cases of common cold. EX. 224E, 0C43 Note - coronaviruses may cause non-A, B or C hepatitis |
| Target antigens: | E1-also called M or matrix protein E2-also called S or Spike protein E3-also called HE or hemagglutinelterose glycoprotein (not present in all coronaviruses) N-nucleocapsid |
| Rhabdovirus Family | |
| Genera: | Vesiliovirus Lyssavirus: (medical and veterinary) rabies |
| Target antigen: | G protein N protein |
| Filoviridue Family: | (Medical) Hemorrhagic fever viruses such as Marburg and Ebola virus |
| Paramyxovirus Family: | |
| Genera: | Paramyxovirus: (Medical and Veterinary) Mumps virus, New Castle disease virus (important pathogen in chickens) Morbillivirus: (Medical and Veterinary) Measles, canine distemper Pneuminvirus: (Medical and Veterinary) Respiratory syncytial virus |
| Orthomyxovirus Family | (Medical) The Influenza virus |
| Bungavirus Family | |
| Genera: | Bungavirus: (Medical) California encephalitis, LA Crosse Phlebovirus: (Medical) Rift Valley Fever Hantavirus: Puremala is a hemahagin fever virus Nairvirus (Veterinary) Nairobi sheep disease Also many unassigned bungaviruses |
| Arenavirus Family | (Medical) LCM, Lassa fever virus |
| Reovirus Family | |
| Genera: | Reovirus: a possible human pathogen Rotavirus: acute gastroenteritis in children Orbiviruses: (Medical and Veterinary) Colorado Tick fever, Lebombo (humans) equine encephalosis, blue tongue |
| Retrovirus Family | |
| Sub-Family: | Oncorivirinal: (Veterinary) (Medical) feline leukemia virus, HTLVI and HTLVII Lentivirinal: (Medical and Veterinary) HIV, feline immunodeficiency virus, equine infections, anemia virus Spumavirinal |
| Papovavirus Family | |
| Sub-Family: | Polyomaviruses: (Medical) BKU and JCU viruses |
| Sub-Family: | Papillomavirus: (Medical) many viral types associated with cancers or malignant progression of papilloma |
| Adenovirus | (Medical) EX AD7, ARD., O.B. - cause respiratory disease - some adenoviruses such as 275 cause enteritis |
| Parvovirus Family | (Veterinary) Feline parvovirus: causes feline enteritis Feline panleucopeniavirus Canine parvovirus |

TABLE 1-continued

| | Porcine parvovirus |
|---|---|
| Herpesvirus Family | |
| Sub-Family: | alphaherpesviridue |
| Genera: | Simplexvirus (Medical) |
| | HSVI, HSVII |
| | Varicellovirus: (Medical - Veterinary) |
| | pseudorabies - varicella zoster |
| Sub-Family- | betaherpesviridue |
| Genera: | Cytomegalovirus (Medical) |
| | HCMV |
| | Muromegalovirus |
| Sub-Family: | Gammaherpesviridue |
| Genera: | Lymphocryptovirus (Medical) |
| | EBV - (Burkitts lympho) |
| | Rhadinovirus |
| Poxvirus Family | |
| Sub-Family: | Chordopoxviridue (Medical - Veterinary) |
| Genera: | Variola (Smallpox) |
| | Vaccinia (Cowpox) |
| | Parapoxivirus - Veterinary |
| | Auipoxvirus - Veterinary |
| | Capripoxvirus |
| | Leporipoxvirus |
| | Suipoxvirus |
| Sub-Family: | Entemopoxviridue |
| Hepadnavirus Family | Hepatitis B virus |
| Unclassified | Hepatitis delta virus |

TABLE 2

Bacterial pathogens

Pathogenic gram-positive cocci include: pneumococcal; staphylococcal; and streptococcal.
Pathogenic gram-negative cocci include: meningococcal; and gonococcal.
Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirillum; listeria monocytogenes; erysipelothrix rhusiopathiae; diphtheria; cholera; anthrax; donovanosis (granuloma inguinale); and bartonellosis.
Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphilis; and leptospirosis.
Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis.
Rickettsial infections include rickettsial and rickettsioses.
Examples of mycoplasma and chlamydial infections include: mycoplasma pneumoniae; lymphogranuloma venereum; psittacosis; and perinatal chlamydial infections.

Pathogenic eukaryotes

Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

---

The invention claimed is:

1. A method of inducing in an individual an immune response against an antigen
wherein said immune response includes both a humoral immune response that includes a mucosal immune response and a cellular immune response that includes antigen specific cytotoxic T lymphocytes;
the method comprising the step of administering by topical or lavage administration to mucosal tissue of said individual, said mucosal tissue selected from the group consisting of rectal, vaginal, urethral, sublingual and buccal, a nucleic acid molecule that is free of an infectious-agent and comprises a nucleotide sequence that encodes said antigen operably linked to regulatory sequences in an amount effective to induce an immune response against said antigen wherein said immune response includes both a humoral immune response that includes a mucosal immune response and a cellular immune response;
wherein said nucleic acid molecule is administered to said individual in a composition that further comprises bupivacaine.

2. A method of inducing in an individual an immune response against an antigen
wherein said immune response includes both a humoral immune response that includes a mucosal immune response and a cellular immune response that includes antigen specific cytotoxic T lymphocytes;
the method comprising the step of administering by topical or lavage administration to mucosal tissue of said individual, said mucosal tissue selected from the group consisting of rectal, vaginal, urethral, sublingual and buccal, a nucleic acid molecule that is free of an infectious-agent and comprises a nucleotide sequence that encodes said antigen operably linked to regulatory sequences in an amount effective to induce an immune response against said antigen wherein said immune response includes both a humoral immune response that includes a mucosal immune response and a cellular immune response;
wherein the antigen is a pathogen antigen and said nucleic acid molecule is administered to said individual in a composition that further comprises bupivacaine.

3. The method of claim 1 wherein the immune response is a therapeutically effective immune response and said nucleic acid molecule is administered in an amount effective to induce a therapeutically effective immune response against said antigen.

4. The method of claim 3 wherein the antigen is a pathogen antigen.

5. The method of claim 4 wherein the pathogen antigen is a viral antigen.

6. The method of claim 5 wherein the viral antigen is an antigen from human immunodeficiency virus.

7. The method of claim 6 wherein the antigen from human immunodeficiency virus comprises an epitope of human immunodeficiency virus protein gp160.

8. The method of claim 1 wherein the immune response is a prophylactically effective immune response and said nucleic acid molecule is administered in an amount effective to induce a prophylactically effective immune response against said antigen.

9. The method of claim 8 wherein the antigen is a pathogen antigen.

10. The method of claim 9 wherein the pathogen antigen is a viral antigen.

11. The method of claim 10 wherein the viral antigen is an antigen from human immunodeficiency virus.

12. The method of claim 11 wherein said viral antigen from human immunodeficiency virus comprise an epitope of human immunodeficiency virus protein gp160.

13. The method of claim 2 wherein the pathogen antigen is a viral antigen.

14. The method of claim 13 wherein the viral antigen is an antigen from human immunodeficiency virus.

15. The method of claim 14 wherein said viral antigen from human immunodeficiency virus comprise an epitope of human immunodeficiency virus protein gp160.

16. The method of claim 1 wherein said nucleic acid molecule is administered to said individual in a composition that comprises a nucleic acid molecule which comprises a nucleotide sequence that encodes a cytokine operatively linked to regulatory sequences which control the expression of said nucleotide sequence; and/or a nucleotide sequence that encodes a lymphokine, operatively linked to regulatory sequences which control the expression of said nucleotide sequence.

17. The method of claim 1, wherein said composition comprises a nucleic acid molecule which comprises a nucleotide sequence that encodes a protein operatively linked to regulatory sequences which control the expression of said nucleotide sequence, wherein said protein is selected from the group consisting of .alpha.-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12.

18. The method of claim 17 wherein said protein is IL-12.

19. The method of claim 2 wherein said nucleic acid molecule is administered to said individual in a composition that comprises a nucleic acid molecule which comprises a nucleotide sequence that encodes a cytokine operatively linked to regulatory sequences which control the expression of said nucleotide sequence; and/or a nucleotide sequence that encodes a lymphokine, operatively linked to regulatory sequences which control the expression of said nucleotide sequence.

20. The method of claim 19 wherein the pathogen antigen is a viral antigen.

21. The method of claim 20 wherein the viral antigen is an antigen front human immunodeficiency virus.

22. The method of claim 21 wherein antigen from human immunodeficiency virus comprise an epitope of human immunodeficiency virus protein gp160.

23. The method of claim 2 wherein said composition comprises a nucleic acid molecule which comprises a nucleotide sequence that encodes a protein operatively linked to regulatory sequences which control the expression of said nucleotide sequence, wherein said protein is selected from the group consisting of .alpha.-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12.

24. The method of claim 23 wherein the pathogen antigen is a viral antigen.

25. The method of claim 23 wherein the viral antigen is an antigen from human immunodeficiency virus.

26. The method of claim 25 wherein antigen from human immunodeficiency virus comprise an epitope of human immunodeficiency virus protein gp160.

27. The method of claim 23 wherein said protein is IL-12.

28. The method of claim 27, wherein the pathogen antigen is a viral antigen.

29. The method of claim 28 wherein the viral antigen is an antigen from human immunodeficiency virus.

30. The method of claim 29 wherein antigen from human immunodeficiency virus comprise an epitope of human immunodeficiency virus protein gp160.

31. The method of claim 1 wherein said mucosal tissue is selected from the group consisting of rectal, vaginal, urethral and said nucleic acid molecule is administered by suppository.

32. The method of claim 31 wherein said mucosal tissue is rectal.

33. The method of claim 31 wherein said mucosal tissue is vaginal.

34. The method of claim 31 wherein said mucosal tissue is urethral.

35. The method of claim 1 wherein said mucosal tissue is selected from the group consisting of sublingual and buccal.

36. The method of claim 35 wherein said mucosal tissue is sublingual.

37. The method of claim 35 wherein said mucosal tissue is buccal.

38. The method of claim 2 wherein said mucosal tissue is selected from the group consisting of rectal, vaginal, urethral and said nucleic acid molecule is administered by suppository.

39. The method of claim 38 wherein said mucosal tissue is rectal.

40. The method of claim 38 wherein said mucosal tissue is vaginal.

41. The method of claim 38 wherein said mucosal tissue is urethral.

42. The method of claim 2 wherein said mucosal tissue is selected from the group consisting of sublingual and buccal.

43. The method of claim 42 wherein said mucosal tissue is sublingual.

44. The meted of claim 43 wherein said mucosal tissue is buccal.

* * * * *

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 1:

AGGCGTCTCG AGACAGAGGA GAGCAAGAAA TG                                  32

(2) INFORMATION FOR SEQ ID NO: 2:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 2:

```
TTTCCCTCTA GATAAGCCAT CCAATCACAC                                      30

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

TTGTTTAACT TTTGATCGAT CCATTCC                                         27

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

GATTTGTATC GATGATCTGA C                                               21

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

TGTAGTAGCA AAAGAAATAG TTAAG                                           25

(2) INFORMATION FOR SEQ ID NO: 6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

AATTCTTAAC TATTTCTTTT GCTAC                                           25

(2) INFORMATION FOR SEQ ID NO: 7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

ATTTGTCGAC TGGTTTCAGC CTGCCATGGC AGGAAGAAGC                            40
```

(2) INFORMATION FOR SEQ ID NO: 8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

ACGACGCGTA TTCTTTAGCT CCTGACTCC                                              29

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

GCTGACGGTA GCGGCCGCAC AATT                                                   24

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GTATTAAGCG GCCGCAATTG TT                                                     22

(2) INFORMATION FOR SEQ ID NO: 11:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

AAAAAGCTTC GCGGATCCGC GTTGCGGCCG CAACCGGTCA CCGGCGACGC GTCGGTCGAC             60

CGGTCATGGC TGGGCCCC                                                          78

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

CCCAAGCTTA GACATGATAA GATACATTG                                              29

(2) INFORMATION FOR SEQ ID NO: 13:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 13:

CTAGCAGCTG GATCCCAGCT TC                                              22

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

GGATTTCTGG GGATCCAAGC TAGT                                            24

(2) INFORMATION FOR SEQ ID NO: 15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

TATAGGATCC GCGCAATGAA AGACCCCACC T                                    31

(2) INFORMATION FOR SEQ ID NO: 16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

ATATGGATCC GCAATGAAAG ACCCCCGCTG A                                    31

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

TAAAGCGGCC GCTCCTATGG CAGGAAGACG                                      30

(2) INFORMATION FOR SEQ ID NO: 18:

(i) SEQUENCE CHARACTERISTICS:
        (A) LENGTH: 34 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 18:

ATTACGCGTC TTATGCTTCT AGCCAGGCAC AATG                34

(2) INFORMATION FOR SEQ ID NO: 19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

ATTACGCGTT TATTACAGAA TGGAAAACAG ATGGCAGGTG          40

(2) INFORMATION FOR SEQ ID NO: 20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

ATTACGCGTT ATTGCAGAAT TCTTATTATG GC                  32

(2) INFORMATION FOR SEQ ID NO: 21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

GAGGCTTGGA GAGGATTATA GAAGTACTGC AAGAGCTG            38

(2) INFORMATION FOR SEQ ID NO: 22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GAATCCTCTC CAAGCCTCAG CTACTGCTAT AGCTGTGGC           39

(2) INFORMATION FOR SEQ ID NO: 23:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

AAAAATAAAG CGGCCGCTCC TATGGCAGGA AGAGAAGCG      39

(2) INFORMATION FOR SEQ ID NO: 24:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

AAAAAATTAC GCGTCTTATG CTTCTAGCCA GGCACAATG      39

(2) INFORMATION FOR SEQ ID NO: 25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

CCCAAGCTTG GGAATGCTCT GCCAGTGTTA C      31

(2) INFORMATION FOR SEQ ID NO: 26:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

GGGGGCCGGA AGGGCACAAT AAAACTGTCT GCTTAC      36

(2) INFORMATION FOR SEQ ID NO: 27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

CCTGATTCAG GTGAAAATAT TGTTGATGCG CTG      33

(2) INFORMATION FOR SEQ ID NO: 28:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

AACATCAATA CAACCTATTA ATTTCCCCTC GTCAAAAATA AGGTTATCAA GTGAGAAATC      60

ACCATCAGTG ACGACTGAAT CCGGTGAGAA TGGCAAAAGT TTATGCATTT C            111

(2) INFORMATION FOR SEQ ID NO: 29:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

CTAGCGCGGG GATCCGCGTT GCGGCCGCAA AAAGTCGACG GGCGACGCGT AAAAA            55

(2) INFORMATION FOR SEQ ID NO: 30:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

GATCTTTTTA CGCGTCGCCC GTCGACTTTT TGCGGCCGCA ACGCGGATCC CCGCG            55

(2) INFORMATION FOR SEQ ID NO: 31:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

ATGTCGACTG GTTTCAGCCT GCCATGGCAG GAAGAAGC            38

(2) INFORMATION FOR SEQ ID NO: 32:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

CCCCACGACG CGTCTATTCT TTAGCTCCTG ACTCC            35

(2) INFORMATION FOR SEQ ID NO: 33:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

TTTGCGGCCG CGTAAGTGGA GAGAGATGGT GCGAG            35

(2) INFORMATION FOR SEQ ID NO: 34:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

CTGGTGGGGC TGTTGGCTCT G                                           21

(2) INFORMATION FOR SEQ ID NO: 35:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

AATTTAATAA GTAAGTAAGT GTCATATGTT TGTTTGAATT CTGCAACAAC TGCTGTTTAT    60

CCATTTTCAG AATTGGGTG                                                79

(2) INFORMATION FOR SEQ ID NO: 36:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

TCGACACCCA ATTCTGAAAA TGGATAAACA GCACTTGTTG CAGAATTCAA ACAAACATAT    60

GACACTTACT TACTTATTA                                                79

(2) INFORMATION FOR SEQ ID NO: 37:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

GGGGTTTTTG GCATATGTA TGAGGGACAA TTGGAGAAGT G                       41

(2) INFORMATION FOR SEQ ID NO: 38:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

AAGCTTGTGG AATTCTTAAT TTCTCTGTCC GGGGTTTTTG GCATATGTA TGAGGGACAT     60

TGGAGAAGTG                                                          70
```

-continued (2) INFORMATION FOR SEQ ID NO: 39:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

CAGTATCTGG CATGGGTAC                      19

(2) INFORMATION FOR SEQ ID NO: 40:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

CCATGCCAGA TACTGGTAC                      19